(12) United States Patent
Kubo et al.

(10) Patent No.: US 12,078,905 B2
(45) Date of Patent: Sep. 3, 2024

(54) ELECTROCHROMIC ELEMENT, OPTICAL FILTER, LENS UNIT, IMAGE PICKUP APPARATUS, AND WINDOW MEMBER

(71) Applicant: CANON KABUSHIKI KAISHA, Tokyo (JP)

(72) Inventors: Wataru Kubo, Inagi (JP); Kenji Yamada, Yokohama (JP); Satoshi Igawa, Fujisawa (JP); Yuto Ito, Koganei (JP); Isao Kawata, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1102 days.

(21) Appl. No.: 16/841,446

(22) Filed: Apr. 6, 2020

(65) Prior Publication Data

US 2020/0241377 A1 Jul. 30, 2020

Related U.S. Application Data

(63) Continuation of application No. PCT/JP2018/035400, filed on Sep. 25, 2018.

(30) Foreign Application Priority Data

Oct. 10, 2017 (JP) ................. 2017-196988
Aug. 8, 2018 (JP) ................. 2018-149516

(51) Int. Cl.
*G02F 1/15* (2019.01)
*B32B 17/10* (2006.01)
(Continued)

(52) U.S. Cl.
CPC .... *G02F 1/15165* (2019.01); *B32B 17/10513* (2013.01); *C07D 241/46* (2013.01); *C07D 401/04* (2013.01); *G02F 2001/15145* (2019.01)

(58) Field of Classification Search
CPC .......... G02F 1/163; G02F 3/16; G02F 1/1521; G02F 1/1533; G02F 1/03; G02F 1/1523;
(Continued)

(56) References Cited

U.S. PATENT DOCUMENTS 5,998,617 A 12/1999 Srinivasa
6,020,987 A 2/2000 Baumann
(Continued)

FOREIGN PATENT DOCUMENTS

CN 103459375 A 12/2013
CN 106632112 A 5/2017
(Continued)

OTHER PUBLICATIONS

Enrique Botana, et al., "Inclusion of Cavitands and Calix[4]arenes into a Metallobridged para-(1H-Imidazo[4,5-f][3,8]phenanthrolin-2-yl)-Expanded Calix[4]arene**", Angewandte Chemie Int. Ed., 2007, vol. 46, pp. 198-201.
(Continued)

*Primary Examiner* — Dawayne Pinkney
(74) *Attorney, Agent, or Firm* — Canon U.S.A., Inc. I.P. Division

(57) ABSTRACT

As an example of an EC element in which vertical color separation is suppressed, the present disclosure provides an EC element including a pair of electrodes, a solvent, an anodic EC compound, and a cathodic EC compound. In the EC element, the difference between a solvation free energy of an oxidized form of the anodic EC compound in water and a solvation free energy of the oxidized form in octanol is 35 kcal/mol or more, and the cathodic EC compound has a substituent containing any one element selected from halogens, sulfur, boron, phosphorus, and silicon.

15 Claims, 5 Drawing Sheets

(51) Int. Cl.

| | |
|---|---|
| *F21V 14/00* | (2018.01) |
| *G02B 26/00* | (2006.01) |
| *G02F 1/1516* | (2019.01) |
| *G02F 1/157* | (2006.01) |
| *G09G 3/19* | (2006.01) |
| *C07D 241/46* | (2006.01) |
| *C07D 401/04* | (2006.01) |
| *G02F 1/1514* | (2019.01) |

(58) Field of Classification Search
CPC ...... G02F 1/1525; G02F 1/155; G02F 1/0316; B60R 1/088; C09K 9/02; H04N 9/3137; H04N 9/22
USPC ................ 359/265–275, 277, 245–247, 242; 345/49, 105, 107; 250/70; 348/814, 817; 438/929; 349/182–186
See application file for complete search history.

(56) References Cited

U.S. PATENT DOCUMENTS

| | | | |
|---|---|---|---|
| 2002/0141032 | A1 | 10/2002 | Guarr |
| 2005/0219678 | A1* | 10/2005 | Lenhard .................. C09K 9/02 549/13 |
| 2006/0103911 | A1 | 5/2006 | Baumann |
| 2017/0114274 | A1 | 4/2017 | Yamada |

FOREIGN PATENT DOCUMENTS

| | | | | |
|---|---|---|---|---|
| EP | 2 259 061 | A2 | 12/2010 | |
| JP | 10-138832 | A | 5/1998 | |
| JP | 2008-521031 | A | 6/2008 | |
| JP | 2012-501007 | A | 1/2012 | |
| JP | 2016-020410 | A | 2/2016 | |
| JP | 2017-21327 | A | 1/2017 | |
| JP | 2017-146590 | A | 8/2017 | |
| WO | WO-0129915 | A2 * | 4/2001 | ............. H01M 4/13 |
| WO | 2005/062110 | A1 | 7/2005 | |
| WO | 2006055391 | A2 | 5/2006 | |
| WO | WO-2017010360 | A1 * | 1/2017 | ............... C09K 9/02 |

OTHER PUBLICATIONS

Susumu Okazaki, The Basics of Computer Simulation, Chapter 7, Kagaku-Dojin Publishing Co., Inc., (2000), p. 121-122.
Brent H. Besler, et al., "Atomic Charges Derived from Semiempirical Methods", Journal of Computational Chemistry, May 1990, vol. 11, pp. 431-439.
J. Chandra Singh and Peter A. Kollman, "An Approach to Computing Electrostatic Charges for Molecules", Journal of Computational Chemistry, Apr. 1984, pp. 129-,145 vol. 5, No. 2.
Nobuyuki Matubayasi and Masaru Nakahara, "Theory of solutions in the energetic representation. I. Formulation", Journal of Chemical Physics, Oct. 15, 2000, vol. 113, pp. 6070-6081.
Shun Sakuraba and Nobuyuki Matubayasi, "ERmod: Fast and Versatile Computation Software for Solvation Free Energy With Approximate Theory of Solutions", Journal of Computational Chemistry, Aug. 2014, vol. 35, pp. 1592-1608.

* cited by examiner

ELECTROCHROMIC ELEMENT, OPTICAL FILTER, LENS UNIT, IMAGE PICKUP APPARATUS, AND WINDOW MEMBER

CROSS-REFERENCE TO RELATED APPLICATIONS

This application is a Continuation of International Patent Application No. PCT/JP2018/035400, filed Sep. 25, 2018, which claims the benefit of Japanese Patent Application No. 2017-196988, filed Oct. 10, 2017 and Japanese Patent Application No. 2018-149516, filed Aug. 8, 2018, all of which are hereby incorporated by reference herein in their entirety.

TECHNICAL FIELD

The present invention relates to an electrochromic element, an optical filter, a lens unit, an image pickup apparatus, and a window member.

BACKGROUND ART

Compounds whose optical properties (e.g., absorption wavelength and absorbance) change through electrochemical redox reactions are referred to as electrochromic (hereinafter, "electrochromic" may be referred to as "EC") compounds. EC elements in which EC compounds are used have been used, for example, in display apparatuses, variable reflectivity mirrors, and variable transmission windows.

In some EC elements, a solution layer containing an anodic EC compound that colors through oxidation and a cathodic EC compound that colors through reduction is used as an EC layer. When such an EC element is driven for a long time in a vertical standing position such that the in-plane direction of electrodes of the EC element is vertical, a phenomenon (segregation) may occur in which an anodic EC compound and a cathodic EC compound are separated from each other in an EC layer. If segregation occurs, color components that make up the color of the colored EC element may be separated from each other to separate the color of the EC element between the upper side and the lower side in the vertical direction (hereinafter, this may be referred to as "vertical color separation").

PTL 1 discloses an EC element in which the viscosity of a solution containing an EC compound is increased by using a thickener. By increasing the viscosity of the solution containing the EC compound, migration of materials in the solution can be inhibited to suppress the occurrence of vertical color separation.

CITATION LIST

Patent Literature

PTL 1: Japanese Patent Laid-Open No. 10-138832

SUMMARY OF INVENTION

However, if the viscosity of a solution containing an EC compound is increased as in Patent Literature 1, migration of materials is inhibited also when a colored state of an EC element is changed, and thus an excessively increased viscosity may reduce the response speed of the EC element. In addition, when, for example, the EC element was driven for a long time at a high coloring concentration, only increasing the viscosity of the EC layer was sometimes insufficient to suppress vertical color separation.

An object of the present invention is to suppress vertical color separation in an EC element by using EC compounds. An electrochromic element in one aspect of the present invention includes a first electrode, a second electrode, and an electrochromic layer disposed between the first electrode and the second electrode. The electrochromic layer contains a solvent, an anodic electrochromic compound, and a cathodic electrochromic compound. The cathodic electrochromic compound has a substituent containing any one element selected from halogens, sulfur, boron, phosphorus, and silicon. The electrochromic element satisfies inequality (1) below.

$$G^{4+}_{H2O} - G^{4+}_{OcOH} \geq 35 \qquad \text{inequality (1)}$$

(In inequality (1), $G^{4+}_{H2O}$ represents a solvation free energy (kcal/mol) of an oxidized form of the anodic electrochromic compound in water, and $G^{4+}_{OcOH}$ represents a solvation free energy (kcal/mol) of the oxidized form of the anodic electrochromic compound in octanol.)

Further features of the present invention will become apparent from the following description of exemplary embodiments with reference to the attached drawings.

DESCRIPTION OF EMBODIMENTS

Hereinafter, embodiments of the present invention will be described with reference to the drawings. The present invention is not limited to the following embodiments. Variations and modifications may be appropriately made to the following embodiments based on common knowledge of those skilled in the art without departing from the spirit of the present invention, and such varied and modified embodiments are also encompassed within the scope of the present invention.

Electrochromic Element

An EC element 1 according to an embodiment will be described with reference to FIG. 1. The EC element 1 is a device that introduces light from the outside and allows the introduced light to pass through at least a part of an EC layer 12 to thereby change properties of outgoing light, typically, light intensity, from those of incident light in at least a predetermined wavelength range.

Figure 1:
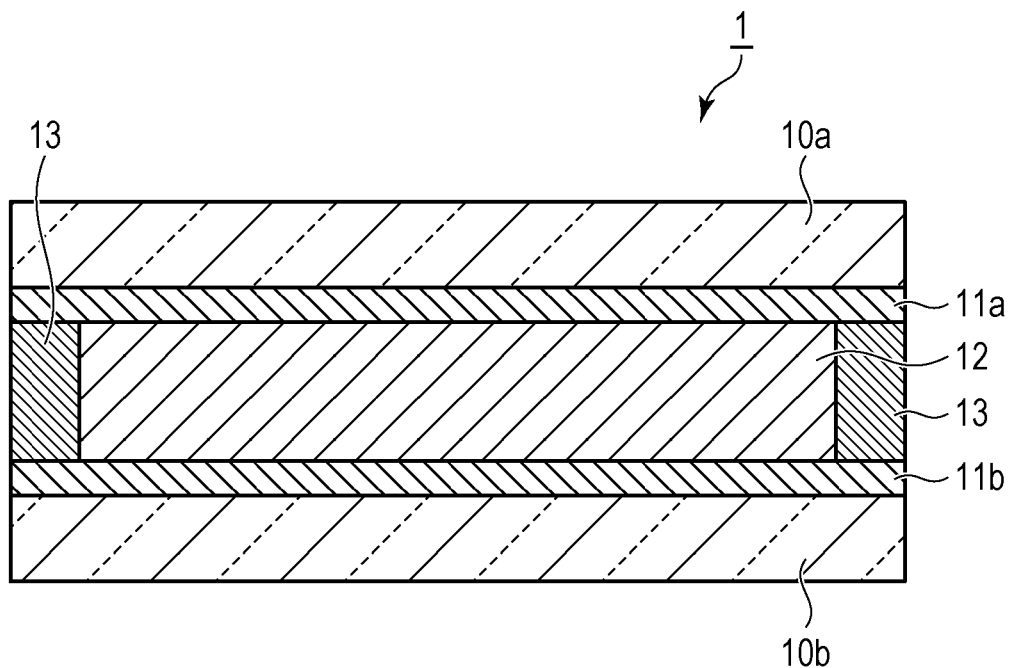
FIG. 1 schematically illustrates an example of an EC element.

FIG. 1 schematically illustrates a configuration of the EC element 1 according to this embodiment. The EC element 1 according to this embodiment includes a first electrode 11a, a second electrode 11b, and an electrochromic layer 12 disposed between the first electrode 11a and the second electrode 11b. The electrochromic layer 12 contains a solvent, an anodic EC compound, and a cathodic EC compound. The difference between a solvation free energy of an oxidized form of the anodic EC compound in water and a solvation free energy of the oxidized form in octanol is 35 kcal/mol or more. The cathodic electrochromic compound has a substituent containing any one element selected from halogens, sulfur, boron, phosphorus, and silicon.

The difference between a solvation free energy in water and a solvation free energy in octanol is an indicator of affinity for a solvent, such as hydrophobicity typified by distribution coefficient. When this value is 35 kcal/mol or more, it indicates that the affinity for a solvent is low, which can be expressed as hydrophobic in the case where the solvent is water.

The EC element in FIG. 1 is an example of an EC element configuration of the present invention, and the EC element of the present invention is not limited thereto. For example, a layer of antireflection coating may be disposed between a substrate 10 and an electrode 11 or between the electrode 11 and the EC layer 12.

Hereinafter, components of the EC element 1 will each be described.

Substrate 10

The EC element 1 may include substrates 10 (a first substrate 10a and a second substrate 10b). At least one of the substrates 10 is preferably a substrate having transparency (transparent substrate). Here, "transparent" means that the light transmittance is 50% or more and 100% or less, more preferably 70% or more and 100% or less. As used herein, "light" means light in a wavelength range used in the EC element. For example, when the EC element is used as an optical filter for a visible-range image pickup apparatus, light means light in the visible range, and when the EC element is used as an optical filter for an infrared-range image pickup apparatus, light means light in the infrared range.

Specifically, the substrates 10 may be made of a colorless or colored glass or a transparent resin. Examples of glasses include optical glass, quartz glass, super white glass, soda-lime glass, borosilicate glass, alkali-free glass, and chemically strengthened glass. Examples of transparent resins include polyethylene terephthalate, polyethylene naphthalate, polynorbornene, polyamide, polysulfone, polyether sulfone, polyether ether ketone, polyphenylene sulfide, polycarbonate, polyimide, and polymethyl methacrylate.

Electrode 11

The electrodes 11 (the first electrode 11a and the second electrode 11b) are preferably composed of a material that is stably present in an operating environment of the EC element 1 and that can immediately cause a redox reaction in response to application of voltage from the outside. The component material of the electrode 11 may be, for example, a transparent conductive material or a metal described later.

At least one of the first electrode 11a and the second electrode 11b is preferably a transparent electrode. Here, "transparent" means that the light transmittance is 50% or more and 100% or less. When at least one of the first electrode 11a and the second electrode 11b is a transparent electrode, light can be efficiently introduced into the EC element 1 from the outside and interacted with the EC compounds in the EC layer 12, thereby reflecting optical properties of the EC compounds on outgoing light.

The transparent electrode may be, for example, a film formed of a transparent conductive material on the substrate 10 or a transparent electrode including a transparent substrate and a metal wire partially disposed thereon. Here, an electrode including a metal wire that is not transparent but that is disposed partially so that the light transmittance is in the above range is called a transparent electrode in the present invention.

Examples of transparent conductive materials include transparent conductive oxides and carbon materials such as carbon nanotubes. Examples of transparent conductive oxides include tin-doped indium oxide (ITO), zinc oxide, gallium-doped zinc oxide (GZO), aluminum-doped zinc oxide (AZO), tin oxide, antimony-doped tin oxide (ATO), fluorine-doped tin oxide (FTO), and niobium-doped titanium oxide (TNO). Of these, FTO or ITO is preferred.

When the electrode 11 is formed of a transparent conductive oxide, the thickness of the electrode 11 is preferably 10 nm or more and 10000 nm or less. In particular, when an FTO or ITO formed to have a thickness of 10 nm or more and 10000 nm or less is used as the electrode 11, high transmittance and chemical stability can be simultaneously achieved.

When the electrode 11 is formed of a transparent conductive oxide, the electrode 11 may have a structure in which sublayers of the transparent conductive oxide are stacked on top of each other. This allows high conductivity and high transparency to be easily achieved.

The metal used as a component material of the electrode 11 is not particularly limited, but electrochemically stable metals, such as silver (Ag), gold (Au), platinum (Pt), and titanium (Ti), are preferably used. The metal wire is preferably disposed in a grid pattern. The electrode provided with the metal wire is typically a flat electrode but may optionally be a curved one.

As described above, at least one of the first electrode 11a and the second electrode 11b is preferably a transparent electrode, but when one of the electrodes is a transparent electrode, the other electrode may be a preferred electrode selected in accordance with an application of the EC element. For example, when the EC element is a transmissive EC element, both the first electrode 11a and the second electrode 11b are preferably transparent electrodes. When the EC element is a reflective EC element, it is preferred that one of the first electrode 11a and the second electrode 11b be a transparent electrode and the other be an electrode that reflects light introduced into the EC element. Furthermore, by forming a reflection layer or a scattering layer between the first electrode 11a and the second electrode 11b, the degree of freedom of optical properties of the other electrode described above can be improved. For example, when a reflection layer or a scattering layer is disposed between the first electrode 11a and the second electrode 11b, the other electrode described above may be a nontransparent electrode or an electrode that absorbs light of interest.

For the arrangement of the first electrode 11a and the second electrode 11b, commonly known electrode arrangements for EC elements can be used. Typically, for example, the first electrode 11a formed on the first substrate 10a and the second electrode 11b formed on the second substrate 10b may be disposed so as to face each other with the EC layer 12 interposed between the first electrode 11a and the second electrode 11b. In this case, the distance (interelectrode distance) between the first electrode 11a and the second electrode 11b is preferably 1 μm or more and 500 μm or less, more preferably 10 µm or more and 100 µm or less. When the interelectrode distance is large, the thickness of the EC layer 12 can be large, and the EC compound in an amount sufficient for the EC element to function effectively can be present in the EC layer 12. As a result, the transmittance in a colored state can be advantageously further reduced. When the interelectrode distance is small, the response speed of the EC element advantageously tends to be high. As described above, when the interelectrode distance is 10 µm or more and 100 µm or less, low transmittance in a colored state and high responsivity can be easily achieved.

Sealing Member

A sealing member 13 is disposed between the first electrode 11*a* and the second electrode 11*b* and bonds the first electrode 11*a* and the second electrode 11*b* together.

The sealing member 13 is preferably formed of a material that is chemically stable, that is poorly permeable to gas and liquid, and that does not inhibit the redox reaction of the EC compounds. For example, inorganic materials such as glass frit, organic materials such as epoxy resins and acrylic resins, and metals can be used. The sealing member 13 may have a function to maintain the distance between the first electrode 11*a* and the second electrode 11*b*, for example, by containing a spacer material. In this case, a space for disposing the EC layer 12 between the electrodes can be created by the first electrode 11*a*, the second electrode 11*b*, and the sealing member 13.

When the sealing member 13 does not have a function to determine the distance between the first electrode 11*a* and the second electrode 11*b*, a spacer having a function to determine and maintain the distance between the electrodes may be separately disposed to maintain the distance between the electrodes. Examples of materials for the spacer include inorganic materials such as silica beads and fiberglass and organic materials such as polyimide, polytetrafluoroethylene, polydivinylbenzene, fluorocarbon rubber, and epoxy resins.

Electrochromic Layer

The EC layer 12 contains a solvent, an anodic EC compound, and a cathodic EC compound. The EC layer 12 is preferably a solution layer in which the anodic EC compound and the cathodic EC compound are dissolved in the solvent. The EC layer 12 may further contain additives such as a supporting electrolyte and a thickener.

Solvent

The solvent can be appropriately selected depending on the intended use in view of, for example, the solubility, vapor pressure, viscosity, and potential window of solutes such as the anodic EC compound and the cathodic EC compound used. The solvent is preferably capable of dissolving the anodic EC compound and the cathodic EC compound used. The solvent is preferably a polar solvent. Specific examples include water and organic polar solvents such as ether compounds, nitrile compounds, alcohol compounds, dimethyl sulfoxide, dimethoxyethane, sulfolane, dimethylformamide, dimethylacetamide, and methylpyrrolidinone. Of these, solvents containing cyclic ethers, such as propylene carbonate, ethylene carbonate, γ-butyrolactone, valerolactone, and dioxolane, are preferred. These solvents containing cyclic ethers are preferred from the viewpoint of the solubility, boiling point, vapor pressure, viscosity, and potential window of the EC compounds. Solvents containing propylene carbonate among cyclic ethers are particularly preferred. The solvent may be an ionic liquid.

A polymer, a gelling agent, or a thickener may further be incorporated into the solvent to make the EC layer 12 more viscous or gelatinous. As the solvent or an electrolytic solution, a polymer electrolyte or a gel electrolyte may be used. Examples of polymers include, but are not limited to, polyacrylonitrile, carboxymethylcellulose, polyvinyl chloride, polyethylene oxide, polypropylene oxide, polyurethane, polyacrylate, polymethacrylate, polyamide, polyacrylamide, polyester, Nafion (registered trademark), and derivatives thereof. When the EC layer 12 is made more viscous or gelatinous, migration of the EC compounds in the EC layer 12 is inhibited. As a result of this, the occurrence of vertical color separation can be further suppressed.

The viscosity of the EC solution may be 10 cP or more and 5000 cP or less, and may be 50 cP or more and 1000 cP or less. The viscosity of the EC solution may be 150 cP or less, and is preferably 100 cP or less, more preferably 65 cP or less. The viscosity of the EC solution may be 20 cP or more, and is preferably 50 cP or more.

The thickener may be present in a weight percentage of 20 wt % or less, provided that the weight of the electrochromic layer is 100 wt %. The weight percentage is preferably 1 wt % or more and 15 wt % or less, more preferably 5 wt % or more and 10 wt % or less.

The EC layer 12 may further contain a supporting electrolyte. The supporting electrolyte is not particularly limited as long as it is a salt that dissociates into ions and has good solubility in the solvent. The supporting electrolyte is preferably a substance stable at an operating potential of the EC element 1. The supporting electrolyte may be a combination of a cation and an anion, each being appropriately selected from various ions. Examples of cations include metal ions such as alkali metal ions and alkaline-earth metal ions and organic ions such as quarternary ammonium ions. Specific examples include $Li^+$, $Na^+$, $K^+$, $Ca^{2+}$, $Ba^{2+}$, tetramethylammonium ion, tetraethylammonium ion, and tetrabutylammonium. Examples of anions include anions of fluorine compounds and halide ions. Specific examples include $ClO_4^-$, $SCN^-$, $BF_4^-$, $AsF_6^-$, $CF_3SO_3^-$, $CF_3SO_2NSO_2CF_3^-$, $PF_6^-$, $I^-$, $Br^-$, and $Cl^-$. A salt compound may be used as the EC compound to allow the EC compound to also function as a supporting electrolyte. Examples of EC compounds that are also salt compounds include viologen derivatives.

The EC layer 12 may be formed by any method, for example, by injecting a liquid containing a solvent and EC compounds into a space provided between the first electrode 11*a* and the second electrode 11*b*, for example, by a vacuum injection method, an atmospheric injection method, or a meniscus method. Specifically, for example, a liquid containing a solvent and EC compounds is injected into a cell constituted by a pair of electrodes 11 and a sealing member 13 through an opening (not illustrated) formed in a part of the electrodes 11 or the sealing member 13, and the opening is sealed with a seal member.

EC Compound

As used herein, the term "EC compound" refers to a compound that is a redox substance and whose optical properties change through a redox reaction in a light wavelength range of interest of the EC element. The optical properties include light absorption properties and light reflection properties and typically mean light absorption properties. The term "redox substance" here means a substance capable of repeatedly undergoing a redox reaction in a predetermined potential range. The EC compound can also be said to be a compound whose light transmittance changes through a redox reaction in a light wavelength range of interest of the EC element. The phrase "optical properties change" here typically means that a light absorption state and a light transmission state are switched to each other. In this case, the EC compound can also be said to be a compound whose light absorption state and light transmission state are switched to each other through a redox reaction.

As used herein, the term "anodic EC compound" refers to an EC compound whose optical properties change through an oxidation reaction in a light wavelength range of interest of the EC element when the EC element 1 is driven. In general, the oxidation reaction is a reaction in which an electron is removed from an EC compound. As used herein, the term "cathodic EC compound" refers to an EC compound whose optical properties change through a reduction reaction in a light wavelength range of interest of the EC element when the EC element 1 is driven. In general, the reduction reaction is a reaction in which an electron is donated to an EC compound. One typical example of the anodic EC compound is a compound whose state changes from a light transmission state to a light absorption state through an oxidation reaction when the EC element 1 is driven. One typical example of the cathodic EC compound is a compound whose state changes from a light transmission state to a light absorption state through a reduction reaction when the EC element 1 is driven. Alternatively, the anodic EC compound and the cathodic EC compound may each be a compound whose state changes from a light absorption state to a light transmission state through an oxidation reaction or a reduction reaction when the EC element 1 is driven. For a better understanding of the change of the light absorption properties of the EC compounds, the following description will be made in the context of a typical example in which the state changes from a light transmission state (decolored state) to a light absorption state (colored state) when the EC element 1 is driven.

By controlling the voltage applied between the first electrode 11a and the second electrode 11b or switching the EC element 1 on and off, the anodic EC compound and the cathodic EC compound undergo an oxidation reaction or a reduction reaction to enter at least two states different from each other. Herein, an EC compound in a state of being oxidized through an oxidation reaction of one or more electrons is called an "oxidized form" of the EC compound, and an EC compound in a state of being reduced through a reduction reaction of one or more electrons is called a "reduced form" of the EC compound. That is to say, the anodic EC compound is a reduced form when the EC element 1 is not driven and becomes an oxidized form when the EC element 1 is driven. The cathodic EC compound is an oxidized form when the EC element 1 is not driven and becomes a reduced form when the EC element 1 is driven.

In some literatures, the state of an EC compound is expressed as changing from an oxidized form to a reduced form (and vice versa) via a neutral form. In the following description, however, oxidized forms and reduced forms are basically described on the basis of the knowledge that a reduced form is formed when an oxidized form is reduced and an oxidized form is formed when a reduced form is oxidized. For example, ferrocene containing divalent iron (neutral as the whole molecule) is a reduced form of ferrocene (an anodic redox substance) when the ferrocene functions as an anodic redox substance. A substance (ferrocenium ion) containing trivalent iron formed as a result of oxidation of the reduced form is an oxidized form of ferrocene (an anodic redox substance), particularly, a first oxidized form. When a dication salt of viologen functions as the cathodic EC compound, the dication salt is an oxidized form of the cathodic EC compound. A monocation salt formed by one-electron reduction of the dication salt is a reduced form of the cathodic EC compound, particularly, a first reduced form.

The EC compounds according to this embodiment are organic compounds. The EC compounds may be low-molecular organic compounds or macromolecular organic compounds but are preferably low-molecular organic compounds having a molecular weight of 2000 or less. The anodic EC compound and the cathodic EC compound are each preferably a compound that is changed from a decolored form to a colored form by driving the EC element 1. The EC compounds may each include a plurality of anodic EC compounds and a plurality of cathodic EC compounds.

The anodic EC compound may be any compound as long as the difference between a solvation free energy of an oxidized form of the anodic EC compound in water and a solvation free energy of the oxidized form in octanol is 35 kcal/mol or more, as described below. Examples of the anodic EC compound include thiophene derivatives, amines having aromatic rings (e.g., phenazine derivatives and triallylamine derivatives), pyrrole derivatives, thiazine derivatives, triallylmethane derivatives, bisphenylmethane derivatives, xanthene derivatives, fluorane derivatives, and spiropyran derivatives. In particular, the anodic EC compound is preferably a low-molecular amine having an aromatic ring, most preferably a dihydrophenazine derivative.

This is because using these compounds as EC compounds allows an EC element having a desired absorption wavelength profile to be readily provided, the EC element having high durability for repeated use. These compounds, when neutral (reduced form), have an absorption peak in the ultraviolet range and no absorption in the visible range, and thus are in a decolored state where the transmittance in the visible range is high. When these molecules become radical cations (oxidized forms) through oxidation reactions, the absorption peak shifts into the visible range, and the molecules enter a colored state. The absorption wavelength of these molecules can be freely designed by increasing or decreasing their π-conjugation length or by changing a substituent to alter the π-conjugated system. Being low-molecular means having a molecular weight of 2000 or less, preferably 1000 or less.

The cathodic EC compound may be any compound that has a substituent containing any one element selected from halogens, sulfur, boron, phosphorus, and silicon, as described below. Examples of the cathodic EC compound include pyridine derivatives such as viologen derivatives and quinone compounds. Of these, pyridine derivatives such as viologen derivatives are most preferably used.

Therefore, the cathodic EC compound is preferably a compound having a pyridine skeleton or a quinone skeleton and having a substituent containing any one element selected from halogens, sulfur, boron, phosphorus, and silicon. More preferably, the cathodic EC compound is a compound having a viologen skeleton and having a substituent containing any one element selected from halogens, sulfur, boron, phosphorus, and silicon.

Still more preferably, the cathodic EC compound is a compound represented by general formula (11) below.

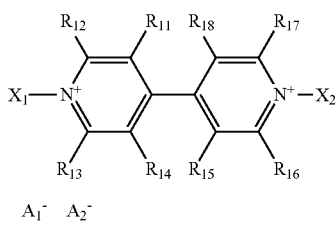

(11)

In general formula (11) above, $X_1$ and $X_2$ are each independently selected from an alkyl group, an aralkyl group, and an aryl group. The alkyl group, the aralkyl group, and the aryl group are optionally substituted. $R_{11}$ to $R_{18}$ are each independently any one of a hydrogen atom, an alkyl group, an aralkyl group, an alkoxy group, an aryl group, a heterocyclic group, a substituted amino group, a halogen atom, and an acyl group. The alkyl group, the alkoxy group, the aralkyl group, the aryl group, and the heterocyclic group are optionally substituted. $A_1^-$ and $A_2^-$ each independently represent a monovalent anion. At least one of $X_1$, $X_2$, and $R_{11}$ to $R_{18}$ is a substituent containing any one element selected from halogens, sulfur, boron, phosphorus, and silicon.

Furthermore, in general formula (11) above, it is particularly preferred that $X_1$ and $X_2$ be substituents containing any one element selected from halogens, sulfur, boron, phosphorus, and silicon.

Cause of Vertical Color Separation

The present inventors synthesized many EC materials and measured and analyzed, under varying conditions, vertical color separation that occurs in EC elements. Consequently, the present inventors revealed that the vertical color separation occurs due to a combination of the following two causes. These two causes will now be described.

(i) Formation of Aggregate Due to Decrease in Affinity for Solvent

When an EC element is driven, an EC compound undergoes a redox (typically, coloration and decoloration) reaction to experience a change in ionic valence. Specifically, when an EC element is driven, an anodic EC compound is oxidized, and its ionic valence is shifted to the plus side, whereas a cathodic EC compound is reduced, and its ionic valence is shifted to the minus side. As a result of this increase and decrease in ionic valence associated with the redox reaction, the EC compounds have a great difference in affinity for a solvent between the oxidized form and the reduced form, typically, a colored form and a decolored form.

The EC compounds are preferably compounds having high solubility in a solvent. In general, the solubility in (affinity for) a solvent of an EC compound is often evaluated in a state where an EC element is not driven, typically, in a decolored state. Therefore, an anodic EC compound whose reduced form has a high affinity for a solvent and a cathodic EC compound whose oxidized form has a high affinity for a solvent are often selected.

However, for the above reason, an EC compound that has a high affinity for a solvent in a state where an EC element is not driven (typically, in a decolored state) may have a low affinity for the solvent in a state where the EC element is driven (typically, in a colored state). For example, in the case where the solubility of an EC compound in a solvent is optimized in a state where an EC element is not driven (typically, in a decolored state), the ionic valence of the EC compound is changed when the EC element is driven, as a result of which the affinity for the solvent decreases. As a result of the decrease in affinity for the solvent, the EC compound becomes energetically stable in the solvent, and thus the anodic EC compound and the cathodic EC compound each form an aggregate. As a result of the formation of the aggregates of the anodic EC compound and the cathodic EC compound, the distribution uniformity of the EC compounds in the EC layer decreases, resulting in an increased likelihood of uneven distribution.

The oxidized form and the reduced form of the EC compounds may also be referred to as a colored form and a decolored form, respectively, in terms of the change in transmittance due to the redox reaction. The shift in ionic valence to the plus side may also be expressed as cationization. The shift in ionic valence to the plus side is meant to include a shift in ionic valence from −2 to −1.

(ii) Difference in Aggregate Density Between Anodic EC Compound and Cathodic EC Compound It is generally known that the density of an organic compound increases when its ionic valence is shifted to the plus side (cationized). As described in (i), an EC compound experiences a change in ionic valence when an EC element is driven, and thus its oxidized form and reduced form, typically, colored form and decolored form, have different densities. Specifically, when an EC element is driven, the ionic valence of an anodic EC compound is shifted to the plus side, thus resulting in an increased density, and the ionic valence of a cathodic EC compound is shifted to the minus side, thus resulting in a decreased density. When there is a difference in density between the EC compounds, one having a higher density is likely to sink by gravity, and one having a lower density is likely to float up.

Due to these two synergistic causes, that is, due to an increased likelihood of uneven distribution of EC compounds due to aggregate formation and an increased likelihood of sinking and floating up due to a difference in aggregate density between the EC compounds, vertical color separation occurs. Specifically, when an EC element is driven continuously for a long time, the color of a colored form of an anodic EC compound is strongly presented on the lower side in the vertical direction, whereas the color of a colored form of a cathodic EC compound, which has a lower density, is strongly presented on the upper side in the vertical direction.

Solution to Vertical Color Separation

The present inventors determined to suppress vertical color separation by applying a solution to "(i) Formation of aggregate due to decrease in affinity for solvent" of the two causes to an anodic EC compound and applying a solution to "(ii) Difference in aggregate density" to a cathodic EC compound. That is to say, the present inventors conceived to combine an anodic EC compound that has a high affinity for a solvent even in a state where an EC element is driven (typically, in a colored state) and a cathodic EC compound that has a density not very different from that of the solvent even in this state. Specifically, as the anodic EC compound, since it is oxidized and hydrophilized to have a decreased affinity for a solvent when an EC element is driven, a compound whose oxidized form has high hydrophobicity was selected to inhibit the formation of an aggregate of the oxidized form. As the cathodic EC compound, since it is reduced and undergoes a change in ionic valence to the minus side to have a decreased density when an EC element is driven, a cathodic EC compound having a high density was selected to inhibit the floating up of a reduced form of the cathodic EC compound in an EC layer. More specifically, a cathodic EC compound having a substituent containing an element that increases the density of organic compounds was selected. The present inventors believed that, regarding the anodic EC compound, this can secure the affinity of the EC compound for a solvent even in a state where an EC element is driven (typically, in a colored state) and inhibit the formation of an aggregate, thereby suppressing vertical color separation. The present inventors believed that, regarding the cathodic EC compound, this can reduce the difference in density between a solvent and an aggregate that can be formed in a state where an EC element is driven (typically, in a colored state), thereby suppressing vertical color separation. Based on this concept, the present inventors synthesized many anodic EC compounds and cathodic EC compounds and combined them to evaluate EC elements, thereby determining the requirement to effectively suppress vertical color separation by the method described above to complete the present invention.

The above requirement that the present inventors have found is to satisfy both the following two conditions.
(a) The difference between a solvation free energy of an oxidized form of an anodic EC compound in water and a solvation free energy of the oxidized form in octanol ((solvation free energy in water)−(solvation free energy in octanol)) is 35 kcal/mol or more.
(b) A cathodic EC compound has a substituent containing any one element selected from halogens, sulfur, boron, phosphorus, and silicon.

In other words, of the above conditions, the condition (a) is to satisfy the following inequality (1).

$$G^{A+}_{H2O} - G^{A+}_{OcOH} \geq 35 \qquad \text{inequality (1)}$$

In inequality (1), $G^{A+}_{H2O}$ represents a solvation free energy (kcal/mol) of an oxidized form of the anodic electrochromic compound in water, and $G^{A+}_{OcOH}$ represents a solvation free energy (kcal/mol) of the oxidized form of the anodic electrochromic compound in octanol.

In the above conditions, "an oxidized form of an anodic EC compound" can also be read as "a colored form of an anodic EC compound".

The present inventors found the above requirement based on the following experimental results.

Figure 2:
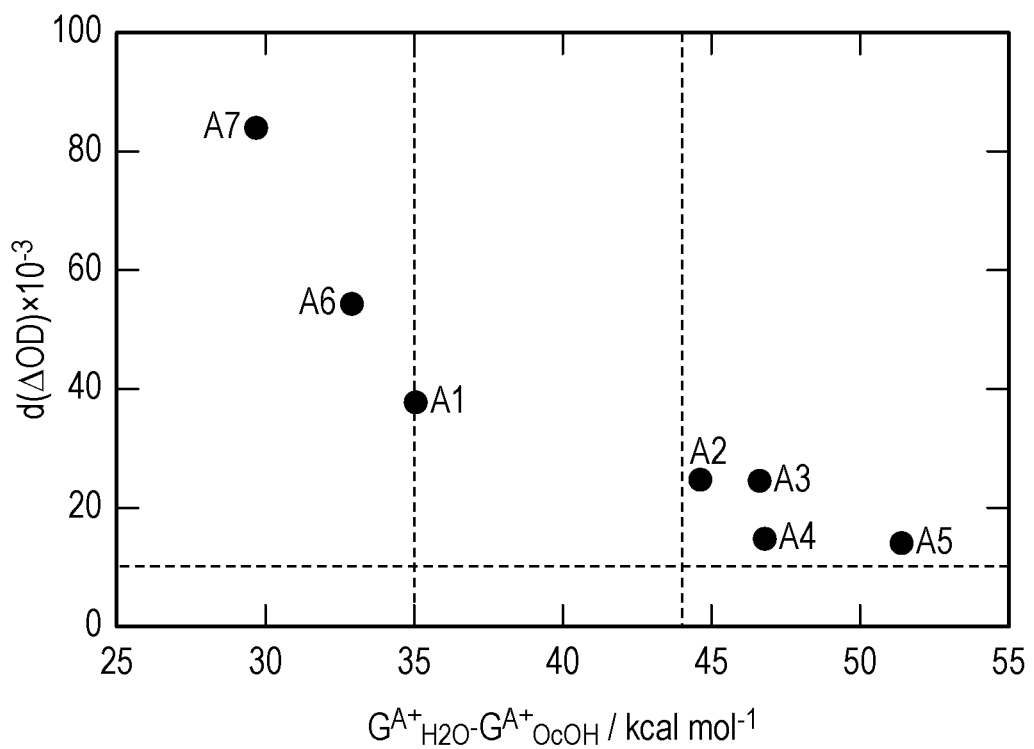
FIG. 2 is a graph showing the relationship between the solvation free energy difference of oxidized forms of anodic EC compounds and the degree of vertical color separation.

FIG. 2 is a graph showing the relationship between the solvation free energy difference $G^{A+}_{H2O} - G^{A+}_{OcOH}$ of anodic EC compounds and the degree of vertical color separation of EC elements in which the anodic EC compounds are used. FIG. 2 is a graph based on the results of experiments in each of which an EC element was produced by using, as the EC layer 12, a solution of an anodic EC compound and a cathodic EC compound in propylene carbonate serving as a solvent and the degree of vertical color separation was measured. In the experiments, the concentrations of the anodic EC compound and the cathodic EC compound in the EC layer 12 were both set to 0.1 mol/L. As the cathodic EC compound, a compound represented by formula (C3) given later was used, and as the anodic EC compound, compounds represented by formulae (A1) to (A9) given later were used. In FIG. 2, the horizontal axis of the graph represents the difference between a solvation free energy of an oxidized form of an anodic EC compound in water and a solvation free energy of the oxidized form in octanol ((solvation free energy in water)-(solvation free energy in octanol)). In FIG. 2, the vertical axis of the graph represents the degree of vertical color separation, and smaller indices d(ΔOD) indicate more effective suppression of vertical color separation. A method of evaluating the degree of vertical color separation will be described later.

From FIG. 2, it can be seen that the degree of vertical color separation tends to decrease as the solvation free energy difference $G^{A+}_{H2O} - G^{A+}_{OcOH}$ of an oxidized form of an anodic EC compound increases. It can be seen that when the solvation free energy difference $G^{A+}_{H2O} - G^{A+}_{OcOH}$ is more than or equal to a predetermined value, vertical color separation can be markedly suppressed. Specifically, it can be seen that when the solvation free energy difference is 35 kcal/mol or more, the degree of vertical color separation can be markedly reduced, and when the solvation free energy difference is 44 kcal/mol or more, the degree of vertical color separation can be more markedly reduced. Therefore, it is more preferable to further satisfy inequality (2) below in addition to inequality (1) above.

$$G^{A+}_{H2O} - G^{A+}_{OcOH} \geq 44 \qquad \text{inequality (2)}$$

However, as a result of further studies by the present inventors, it has been found that there is a limit to how effectively vertical color separation can be suppressed only by focusing on the solvation free energy difference $G^{A+}_{H2O} - G^{A+}_{OcOH}$ and selecting an anodic EC compound as described above. This is because even in the case where a compound less likely to form an aggregate when oxidized (typically, when colored) is used as the anodic EC compound, the entire EC element undergoes vertical color separation if the cathodic EC compound is likely to form an aggregate when reduced (typically, when decolored). Thus, the present inventors conducted a study also on cathodic EC compounds and investigated the degree of vertical color separation occurring when elements that increase the density of organic compounds were introduced into substituents thereof.

Figure 3:
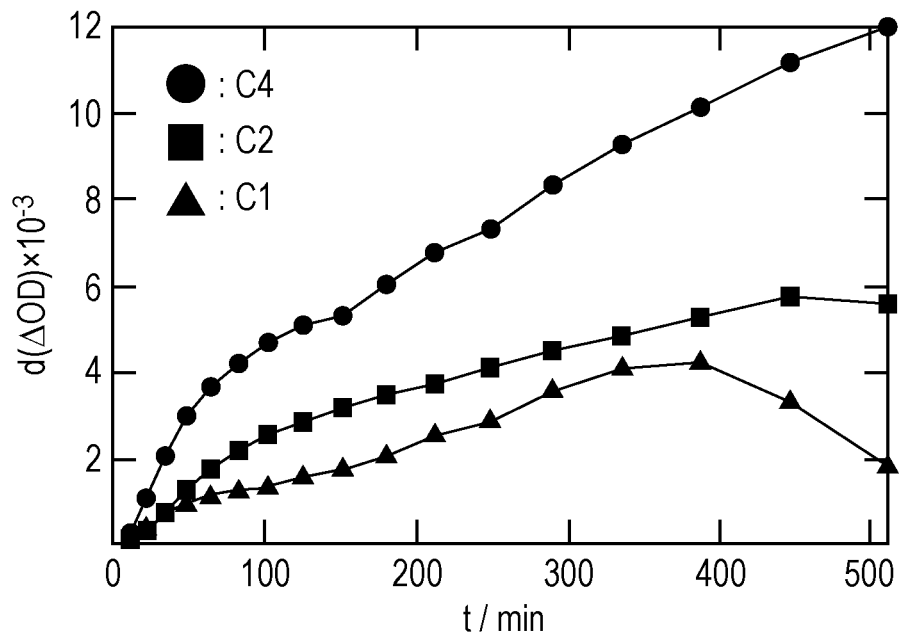
FIG. 3 is a graph showing the results of measurements of the change with time in vertical color separation of three EC elements in which cathodic EC compounds having different substituents are used.

FIG. 3 is a graph showing the results of measurements of the change with time in the degree of vertical color separation of three EC elements in which cathodic EC compounds having different substituents are used. FIG. 3 is a graph based on the results of experiments in each of which an EC element was produced by using, as the EC layer 12, a solution of an anodic EC compound and a cathodic EC compound in propylene carbonate serving as a solvent and the degree of vertical color separation was measured. In the experiments, the concentrations of the anodic EC compound and the cathodic EC compound in the EC layer 12 were set to 0.1 mol/L. As the anodic EC compound, a compound represented by formula (A1) given later was used. As the anodic EC compound, compounds represented by formulae (C1), (C2), and (C4) given later were used. In FIG. 3, a compound represented by formula (C1), plotted with a sign ♦, and a compound represented by formula (C2), plotted with a sign ■, each have a substituent containing fluorine, which is an element that increases the density of organic compounds.

In FIG. 3, a compound represented by formula (C4), plotted with a sign ●, does not have a substituent containing an element that increases the density of organic compounds and is a cathodic EC compound for comparison having unsubstituted alkyl. In FIG. 3, the horizontal axis of the graph represents the elapsed time since the start of continuous coloring drive, and the vertical axis of the graph represents the degree of vertical color separation. Smaller d(ΔOD) values indicate more effective suppression of vertical color separation.

From FIG. 3, it can be seen that the degree of vertical color separation is decreased by introducing an element that increases the density of organic compounds into a substituent of a cathodic EC compound.

Here, examples of the element that increases the density of organic compounds include halogens, sulfur, boron, phosphorus, and silicon. Of these, halogens are preferred, and fluorine is more preferred.

The above studies demonstrate that vertical color separation cannot be effectively suppressed such that the maximum value of d(ΔOD) is as low as 0.01 or less until a compound that is less likely to form an aggregate when an EC element is driven is employed as an anodic EC compound and a compound having a substituent that increases the density of compounds is employed as a cathodic EC compound. More specifically, the degree of vertical color separation cannot be effectively suppressed such that the value of d(ΔOD) is as low as 0.01 or less until both the above two conditions (a) and (b) are satisfied.

Method of Evaluating Degree of Vertical Color Separation

Figure 4:
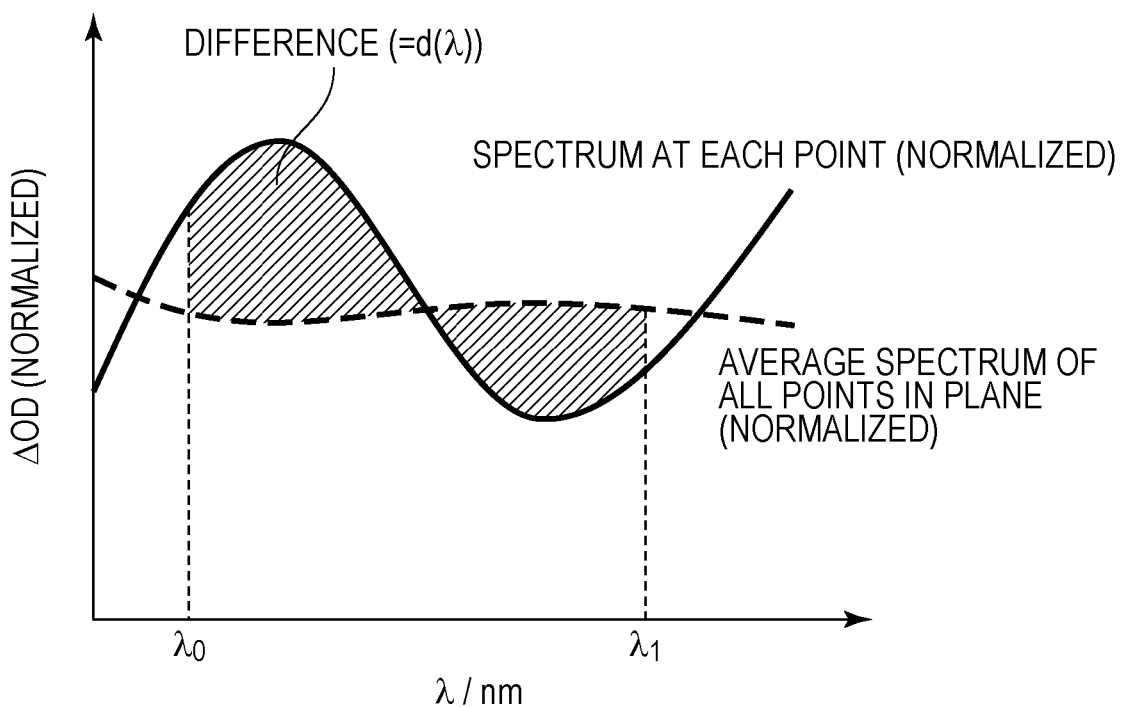
FIG. 4 is a graph illustrating a method of evaluating vertical color separation.

A method of evaluating the degree of vertical color separation will be described with reference to FIG. 4.

A transmissive EC element was driven, and light was transmitted through the EC element. The spectrum of the transmitted light was measured two-dimensionally in an element plane of the EC element, that is, at points in the element plane of the EC element. This measurement of the spectrum of transmitted light was performed over time, showing that the average spectrum, which is the average of spectra at all the points in the element plane of the EC element at each time, did not substantially vary according to time (according to the passage of time). Thus, in this DESCRIPTION, the average spectrum of all the points in the plane was used as a reference spectrum, and the degree of vertical color separation was evaluated on the basis of the deviation of a spectrum at each point in the plane from the reference spectrum.

Specifically, first, the reference spectrum and spectra at points in the plane were each normalized to eliminate the influence of concentration variation (which has no influence on vertical color separation) of the whole EC compound in the EC layer in the in-plane direction of the element. The normalization was performed such that the average optical density variation (ΔOD) was 1 in a predetermined wavelength range (425 nm to 700 nm in this case). For each of these normalized spectra at the points in the plane, the value of d(ΔOD) was calculated by formula (5) below, where D(λ) is a difference from the normalized reference spectrum.

$$d(\Delta OD) = \sqrt{\frac{1}{\lambda_1 - \lambda_0} \int_{\lambda_0}^{\lambda_1} (D(\lambda))^2 d\lambda}$$

Here, in formula (5), $\lambda_0$ represents the lower limit (nm, 425 nm in this case) of a light wavelength range of interest, and $\lambda_1$ represents the upper limit (nm, 700 nm in this case) of the light wavelength range of interest. The value of d(ΔOD) indicates an average divergence of the above normalized spectra at the points in the plane from the reference spectrum, and the larger the value is, the more the spectra of transmitted light at the points are deviated from the reference spectrum. Thus, the value of d(ΔOD) was calculated for each of the spectra at the points in the plane at each time (elapsed time), and its average was calculated. Using a maximum value within an evaluation time period (typically, within 24 hours) of the average value of d(ΔOD) calculated at each time, the degree of vertical color separation of the EC element was evaluated.

Examples of applications of the EC element 1 according to this embodiment include display apparatuses, variable reflectivity mirrors, variable transmission windows, and optical filters. If vertical color separation occurs in these applications, the color balance of transmitted light or reflected light on the upper side and the lower side of the EC element plane will change unexpectedly, which is not preferred in all the applications.

The value of d(ΔOD) will be discussed in the context of using the EC element as an optical filter, particularly, an ND filter of a camera, for example. If vertical color separation occurs in the EC element used as an ND filter, a captured image will have a difference in tint between the upper side and the lower side. Specifically, in the case where each EC compound is colored by driving the EC element, typically, the color of the colored cathodic EC compound is strongly presented on the upper side of a filter, and the color of the colored anodic EC compound is strongly presented on the lower side of the filter. As a result, in the captured image, the color of the colored cathodic EC compound is strongly presented on the lower side, and the color of the colored anodic EC compound is strongly presented on the upper side of the image. This is because an image pickup element reads light beams that are focused after passing through a lens and thus the upper side and the lower side of an image are reverse to those of the filter. For this reason, when the degree of vertical color separation is high, acquired images disadvantageously have significantly degraded quality.

Known cathodic EC compounds include viologen compounds, and known anodic EC compounds include dihydrophenazine compounds. When these are used as the EC compounds, in an image that has undergone the vertical color separation described above, green to blue is strongly presented on the lower side of the image, and red is strongly presented on the upper side of the image. That is to say, the image has significantly degraded quality.

As described above, when the EC element is used in applications such as optical filters, it is required that the degree of vertical color separation be reduced. Specifically, if the value of d(ΔOD) is controlled to be 0.01 or less by the approach regarding the EC compounds, the quality of acquired images can be maintained even when the EC element is used as an optical filter. This can prevent phenomena, for example, in which a person's face looks blue in a lower part of a display and in which an image of sky looks purplish in an upper part of the display.

Concentration of EC Compounds

Figure 5:
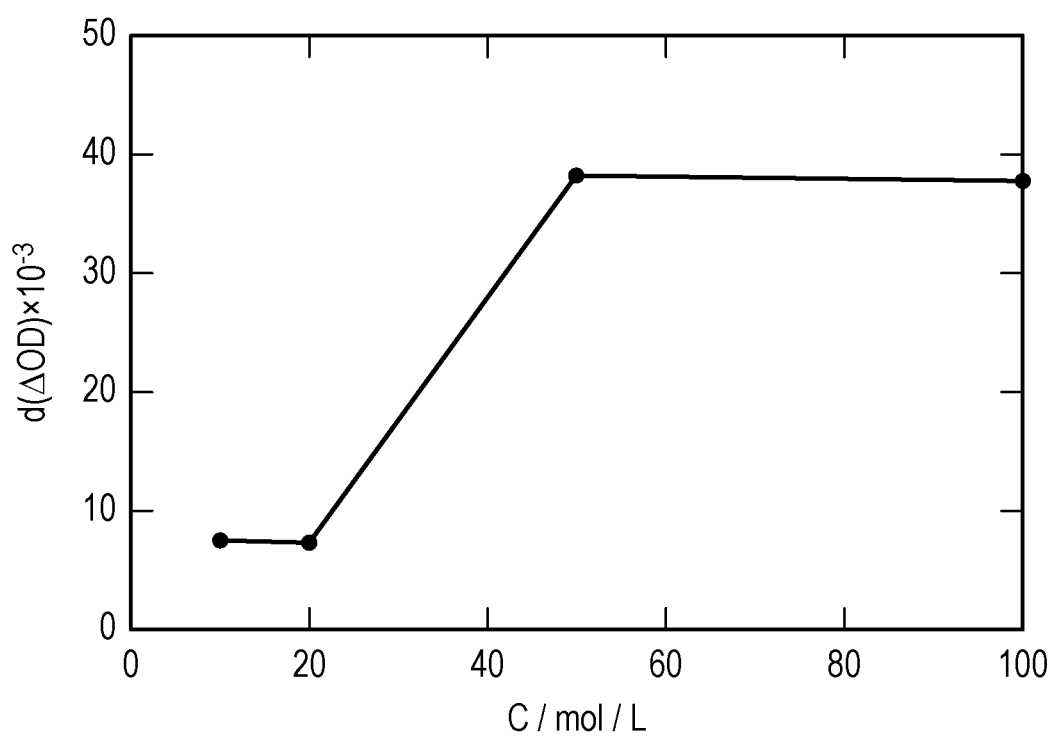
FIG. 5 is a graph showing the relationship between the concentration of EC compounds and the degree of vertical color separation.

FIG. 5 is a graph showing the relationship between the concentration C (mol/L) of an anodic EC compound and a cathodic EC compound and the degree of vertical color separation. FIG. 5 is a graph related to an EC element in which a compound represented by formula (A1) given later is used as the anodic EC compound, a compound represented by formula (C3) given later is used as the cathodic EC compound, and a solution of these compounds in propylene carbonate, serving as solvent, is used as an EC layer. Here, the concentrations of the anodic EC compound and the cathodic EC compound in the EC layer are each expressed in C (mol/L). In FIG. 5, the horizontal axis of the graph represents the concentration C (mol/L) of each of the anodic EC compound and the cathodic EC compound, and the vertical axis of the graph represents the degree of vertical color separation described above.

FIG. 5 shows that when the concentration C of the anodic EC compound and the cathodic EC compound is 0.05 mol/L or more, vertical color separation occurs prominently. As described above, one of the causes of vertical color separation is as follows: the affinities of EC compounds for a solvent decrease when an EC element is driven, and the EC compounds form aggregates. The formation of an aggregate is greatly influenced by the concentration of a component that forms the aggregate. Specifically, an aggregate is more readily formed when the concentration of a component that forms the aggregate is higher, and when the concentration exceeds a threshold, the aggregate formation progresses rapidly. Here, the degree of aggregate formation is high and vertical color separation is strongly exhibited in a region where the concentration of the EC compounds in the EC layer is 0.05 mol/L or more.

In the EC element, when the concentration of the EC compounds in the EC layer is high, the amount of change in optical properties between when the EC element is driven and when not driven tends to be large. However, as described above, when the concentration of the EC compounds in the EC layer is high, aggregate formation is likely to occur, and thus vertical color separation is also likely to occur. However, according to this embodiment, the aggregate formation can be inhibited by appropriately selecting the affinities of the anodic EC compound and the cathodic EC compound for a solvent. Thus, even when the concentration of the anodic EC compound and the cathodic EC compound is as high as 0.05 mol/L or more, the aggregate formation at the time when the EC element is driven can be inhibited to suppress vertical color separation.

Method of Calculating Solvation Free Energy

A method of calculating the solvation free energy of an oxidized form or a reduced form (typically, a colored form) of an EC compound will be described below.

The solvation free energy in a state where a molecule A is dissolved in a solvent composed of a molecule B can be calculated by performing sampling of the following three equilibrium states by molecular dynamics calculations and then using an energy representation method.

(i) Sampling of isothermal-isobaric equilibrium state of solution system X constituted by one molecule A and multiple molecules B
(ii) Sampling of isothermal-isobaric equilibrium state of solvent system Y constituted by multiple molecules B
(iii) Sampling of isothermal-isochoric equilibrium state of system Z constituted by one molecule A Sampling of Equilibrium State by Molecular Dynamics Calculations A sample of an equilibrium state by molecular dynamics calculations can be obtained by arranging molecules of interest in a unit cell to which a periodic boundary condition is applied, calculating the force acting between atoms contained in each molecule at a time interval, and calculating the loci of all the atoms relative to the time evolution. The molecular dynamics calculations are described in Technical Literature 1 ("The Basics of Computer Simulation", Susumu Okazaki, Kagaku-Dojin Publishing Co., Inc. (2000)). Sampling of an equilibrium state by molecular dynamics calculations can be performed using GROMACS-5.1, which is molecular dynamics simulation software.

To perform molecular dynamics calculations, a parameter called a "force-field parameter" for defining an interaction between atoms needs to be set in advance. The force-field parameter is constituted by two parameters, an electrostatic force-field parameter and a non-electrostatic force-field parameter.

An assigned charge of each atom is used as the electrostatic force-field parameter. The assigned charge of each atom can be obtained by performing charge fitting on an electrostatic potential calculated by quantum chemical calculations. The Kohn-Sham method can be used for the quantum chemical calculations for calculating the electrostatic potential, and in the calculations, B3LYP can be used as an exchange-correlation functional, and 6-31G* as a basis function. 6-31G* is obtained by adding a polarization function to 6-31G. The charge fitting can be performed using an evaluation score based on the Merz-Singh-Kollman method. The above quantum chemical calculations can be performed using Gaussian 09 Revision D. 01 (M. J. Frisch, et al., Gaussian, Inc., Wallingford CT, 2013.). The Merz-Singh-Kollman method is described in Technical Literature 2 (B. H. Besler, et al., J. Comp. Chem. 11, 431 (1990).) and Technical Literature 3 (U. C. Singh, et al., J. Comp. Chem. 5, 129 (1984).).

The general Amber force field (GAFF), which is commonly used for organic molecules, is used as the non-electrostatic force-field parameter.

The molecular dynamics calculations are composed of three stages: a compression process, an equilibration process, and Production Run. The compression process is performed to form an appropriate molecular assembly. The equilibration process is performed to guide a calculation system into a thermodynamic equilibrium state. In Production Run, sampling of the equilibrium state is performed.

Calculation conditions used in the compression process are as follows: simulation time, 40 ps; temperature, 700 K; compression ratio setting, 0.000045; atmospheric pressure setting, 10000 atm. The compression process is an isothermal-isobaric simulation using the Berendsen method.

Calculation conditions used in the equilibration process are as follows: simulation time, 5 ns; temperature, 300 K; compression ratio setting, 0.000045; atmospheric pressure setting, 1 atm. The equilibration process is an isothermal-isobaric simulation using the Berendsen method.

Calculation conditions used in the Production Run are as follows: simulation time, 20 ns; compression ratio setting, 0.000045; atmospheric pressure setting, 1 atm. The Production Run is an isothermal-isobaric simulation using the Berendsen method.

Calculation of Free Energy by Energy Representation Method

According to the energy representation method performed after the sampling of an equilibrium state by molecular dynamics calculations, an interaction between a solvent molecule B and a solute molecule A is evaluated, and the solvation free energy at the time when the molecule A is dissolved in a solvent composed of the molecule B can be finally calculated. The energy representation method is described in Technical Literature 4 (N. Matubayasi et al, J. Chem. Phys. 113, 6070-6081 (2000).) and Technical Literature 5 (S. Sakuraba, et al, J. Comput. Chem. 35, 1592-1608 (2014).). The calculation of free energy by the energy representation method can be performed using ERmod-0.3, which is free energy calculation software.

Method of Driving EC Element

The EC element according to this embodiment may be driven by any method, preferably by controlling the transmittance of the EC element by pulse width modulation. For example, the transmittance of the EC element is controlled by changing the ratio of a voltage application period relative to one cycle of a pulse voltage waveform while maintaining the transmittance of the EC element without changing the peak value of the pulse voltage waveform.

This ratio of a voltage application period relative to one cycle is defined as the Duty ratio. When the Duty ratio for pulse driving is maintained, the coloring of EC materials increases during the voltage application period, and the coloring of the EC materials decreases during the rest period. When the EC element is driven at a constant voltage from a driving power supply without changing the Duty ratio, the change in absorbance is saturated via a transient state, and the saturated absorbance is maintained. The absorbance can be decreased by setting the Duty ratio to be smaller than the immediately previous Duty ratio. The absorbance can be increased by setting the Duty ratio to be larger than the immediately previous Duty ratio. Here, when one cycle of control signals is long, an increase or a decrease in absorbance may be visually observed. Thus, one cycle is preferably 100 milliseconds or less, more preferably 10 milliseconds or less.

Effects

According to the EC element according to this embodiment, the anodic EC compound contained in the EC layer can be inhibited from forming an aggregate when the EC element is driven. In addition, the cathodic EC material can be inhibited from floating up due to a difference in density in the EC layer when the EC element is driven. Thus, even when the EC element is continuously driven for a long time in a vertical standing position, vertical color separation, which is a phenomenon in which the anodic EC compound and the cathodic EC compound are vertically separated from each other, can be suppressed. According to this embodiment, vertical color separation can be suppressed without greatly increasing the viscosity of the EC layer, and thus vertical color separation can be suppressed while suppressing a decrease in element responsivity. Vertical color separation can be further suppressed by appropriately increasing the viscosity of the EC layer, and thus vertical color separation can also be further suppressed while securing the element responsivity.

Optical Filter, Image Pickup Apparatus, and Lens Unit

The EC element 1 can be used for optical filters. An optical filter 101 according to another embodiment of the present invention illustrated in FIG. 6 includes the EC element 1 and an active element connected to the EC element 1. The active element adjusts the amount of light transmitted through the EC element. Specific examples of such an element include switching elements for controlling the transmittance of the EC element. Examples of switching elements include TFTs and MIM elements. TFTs are also referred to as thin-film transistors, and semiconductors and oxide semiconductors are used as component materials thereof. Specific examples include semiconductors composed of materials such as amorphous silicon, low-temperature polysilicon, and InGaZnO.

The EC element 1 can be used for image pickup apparatuses and lens units. An image pickup apparatus 103 according to another embodiment of the present invention illustrated in FIG. 6 includes the above-described optical filter 101 including the EC element 1 and a light-receiving element 110 that receives light that has passed through the optical filter 101.

A lens unit 102 according to another embodiment of the present invention includes the above-described optical filter 101 including the EC element 1 and an image pickup optical system. The image pickup optical system is preferably a lens group including a plurality of lenses. The optical filter 101 may be disposed such that light that has passed through the optical filter 101 passes through the image pickup optical system, or may be disposed such that light that has passed through the image pickup optical system passes through an optical filter 101. The optical filter 101 may be disposed between the plurality of lenses. The optical filter 101 is preferably disposed on the optical axis of the lenses. The optical filter 101 can adjust the amount of light that passes through or has passed through the image pickup optical system.

Figure 6A:
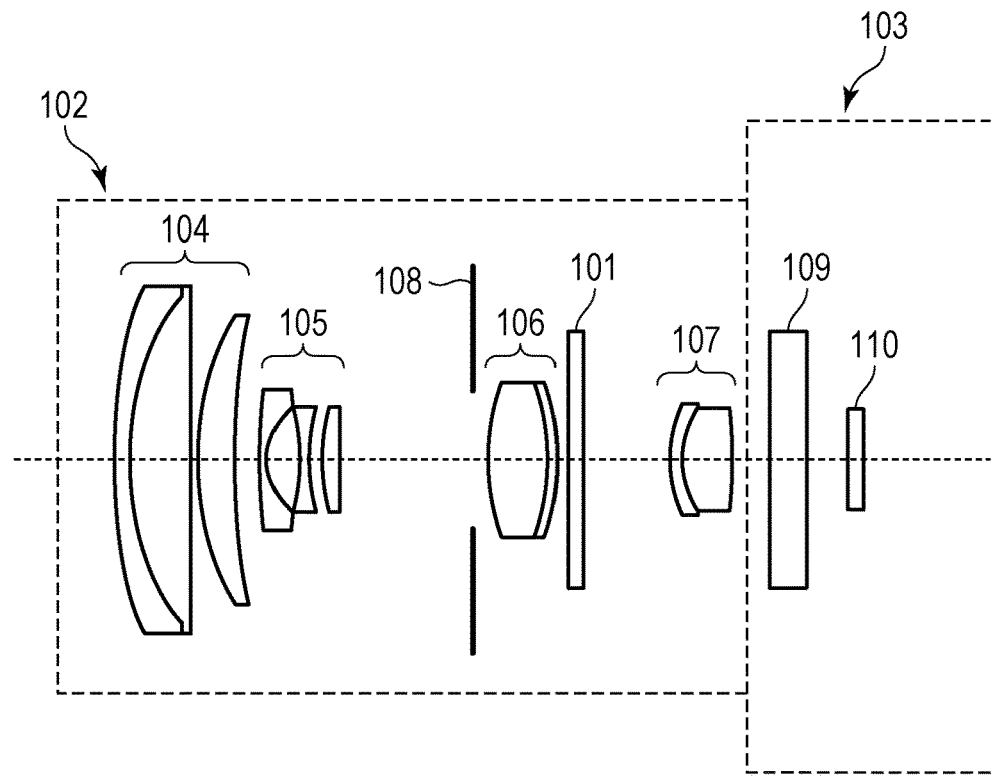
FIG. 6A schematically illustrates an example of an image pickup apparatus and a lens unit.
Figure 6B:
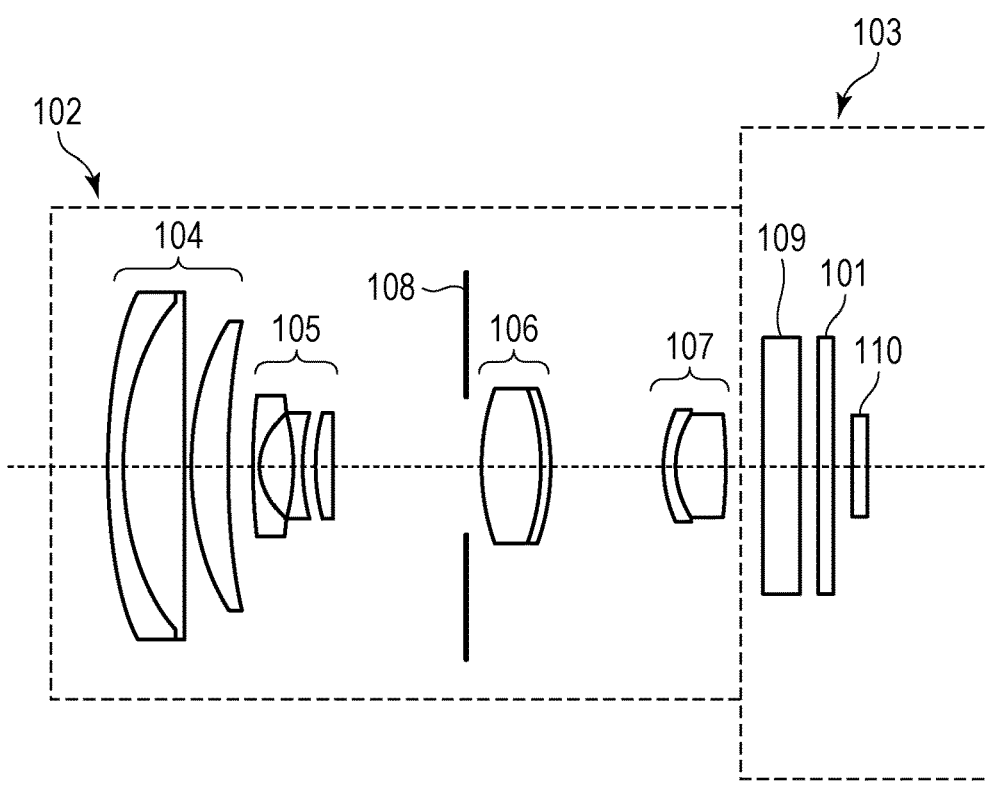
FIG. 6B schematically illustrates an example of an image pickup apparatus and a lens unit.

FIG. 6 schematically illustrates examples of an image pickup apparatus including the optical filter 101 and a lens unit including the optical filter 101. FIG. 6A illustrates an image pickup apparatus including the lens unit 102 including the optical filter 101, and FIG. 6B illustrates the image pickup apparatus 103 including the optical filter 101. As illustrated in FIG. 6A, the lens unit 102 is detachably connected to an image pickup unit 103 through a mounting member (not illustrated).

The lens unit 102 includes a plurality of lenses or lens groups. For example, in FIG. 6A, the lens unit 102 is a zoom lens of rear-focus type in which focusing is carried out behind a stop. The lens unit 102 includes four lens groups: a first lens group 104 having positive refractive power, a second lens group 105 having negative refractive power, a third lens group 106 having positive refractive power, and a fourth lens group 107 having positive refractive power, which are disposed in this order from the object side (the left side of the drawing plane). The magnification is varied by changing the distance between the second lens group 105 and the third lens group 106, and focusing is carried out by moving some of the lenses of the fourth lens group 107. For example, the lens unit 102 includes an aperture stop 108 disposed between the second lens group 105 and the third lens group 106 and the optical filter 101 disposed between the third lens group 106 and the fourth lens group 107. Light passing through the lens unit 102 passes through the lens groups 104 to 107, the aperture stop 108, and the optical filter 101, and the amount of light can be adjusted by using the aperture stop 108 and the optical filter 101.

The configuration in the lens unit 102 may be changed as appropriate. For example, the optical filter 101 can be disposed in front of (the object side) or behind (the image pickup unit 103 side) the aperture stop 108. The optical filter 101 may be disposed in front of the first lens group 104 or may be disposed behind the fourth lens group 107. Disposing the optical filter 101 at a position where light converges is advantageous in that, for example, the optical filter 101 may have a small area. The type of the lens unit 102 can be appropriately selected. The lens unit 102 may be not only of rear-focus type but also of inner-focus type in which focusing is carried out in front of a stop or of other types. In addition to zoom lenses, special lenses such as fisheye lenses and macro lenses can be appropriately selected.

The image pickup unit 103 includes a glass block 109 and a light-receiving element 101. The glass block 109 is, for example, a low-pass filter, a face plate, or a color filter. The light-receiving element 110 is a sensor that receives light that has passed through the lens unit 102 and may be an image pickup element such as a CCD or a CMOS. The light-receiving element 110 may also be a light sensor such as a photodiode, and a light sensor that acquires and outputs information about light intensity or wavelength can be appropriately used.

When the optical filter 101 is incorporated in the lens unit 102 as illustrated in FIG. 6A, a driver such as an active element may be disposed within the lens unit 102 or may be disposed outside the lens unit 102. When the driver is disposed outside the lens unit 102, the driver outside the lens unit 102 and the EC element in the lens unit 102 are connected to each other through a wire to control driving.

As illustrated in FIG. 6B, the image pickup apparatus itself may include the optical filter 101. The optical filter 101 is disposed at an appropriate position within the image pickup unit 103, and the light-receiving element 110 is disposed so as to receive light that has passed through the optical filter 101. In FIG. 6B, for example, the optical filter 101 is disposed immediately in front of the light-receiving element 110. When the image pickup apparatus itself includes the optical filter 101, the lens unit 102 itself connected to the image pickup apparatus need not include the optical filter 101, thus enabling an image pickup apparatus that includes an existing lens unit and is able to modulate light.

Such an image pickup apparatus can be applied to products including a combination of light-amount adjustment and a light-receiving element. For example, the image pickup apparatus can be used for cameras, digital cameras, video cameras, and digital video cameras, and can be applied to products containing an image pickup apparatus, such as cellular phones, smartphones, PCs, and tablets.

Using the optical filter according to this embodiment as a light modulation member enables the amount of light modulation to be appropriately varied with a single filter, leading to advantages such as reduction in the number of members and space saving.

According to the optical filter, the lens unit, and the image pickup apparatus according to this embodiment, vertical color separation in an EC element can be suppressed. Thus, degradation of quality of an image obtained by capturing light transmitted through or reflected by the optical filter can be suppressed.

Window Member

Figure 7A:
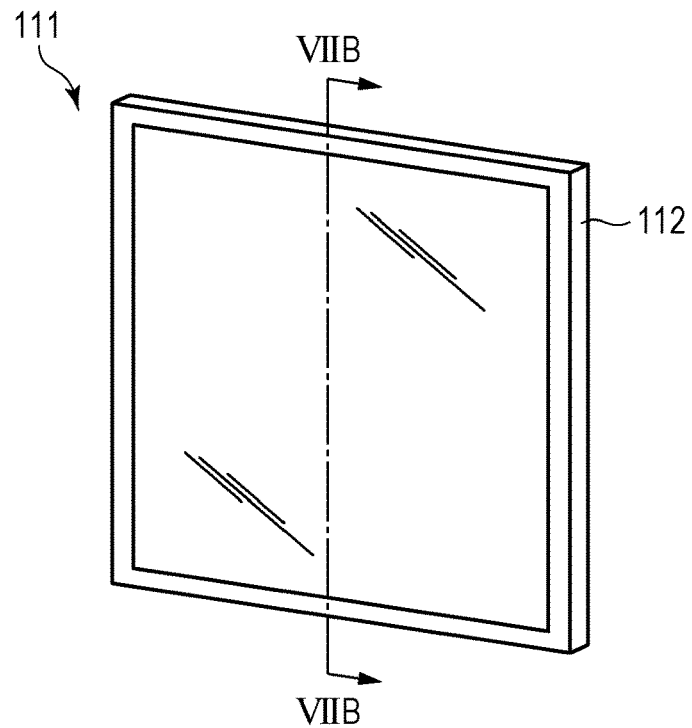
FIG. 7A schematically illustrates an example of a window member.
Figure 7B:
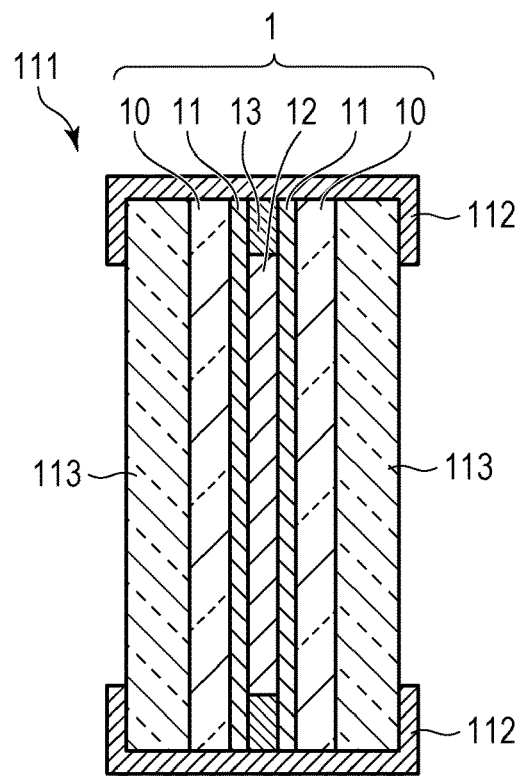
FIG. 7B schematically illustrates an example of a window member.

A window member according to another embodiment of the present invention includes the EC element 1 and an active element connected to the EC element. FIG. 7 schematically illustrates an example of a window member according to this embodiment. FIG. 7A is a perspective view, and FIG. 7B is a sectional view taken along line VIIB-VIIB in FIG. 7A.

A window member 111 in FIG. 7 is a light modulation window and includes the EC element 1, transparent plates 113 (a pair of substrates) that sandwiches the EC element 1, and a frame 112 that surrounds the entirety for integration. The active element adjusts the amount of light transmitted through the EC element 1 and may be directly or indirectly connected to the EC element 1. The active element may be integrated inside the frame 112 or may be disposed outside the frame 112 and connected to the EC element 1 through a wire.

The transparent plates 113 may be made of any material that has high light transmittance and is preferably made of a glass material in view of the use as a window. Although the EC element 1 is a constituent member independent of the transparent plates 113 in FIG. 7, for example, the substrates 10 of the EC element 1 may be considered as the transparent plates 113.

The frame 112 may be made of any material, and all types of frames that cover at least a part of the EC element 1 and have an integrated form may be used.

The light modulation window, which can also be referred to as a window member including an electronic curtain, allows a sufficient amount of incident light to pass therethrough when the EC element 1 is in a decolored state, and exhibits optical properties so as to reliably block and modulate incident light when the EC element 1 is in a colored state. The window member according to this embodiment can be used, for example, in an application where the amount of sunlight that enters a room during the daytime is adjusted. The light modulation window can be applied to the adjustment of the amount of heat as well as the amount of sunlight and thus can be used to control the brightness and temperature in a room. The light modulation window can also be used as a shutter to prevent the inside of a room from being viewed from the outside. The light modulation window can be applied not only to glass windows for buildings but also to windows of vehicles such as automobiles, trains, airplanes, and ships, filters for display surfaces of clocks and cellular phones, and the like.

EXAMPLES

The present invention will now be described in more detail with reference to examples, but the present invention is not limited to these examples.

Specific Examples of EC Compounds Used in Solution to Vertical Color Separation

Anodic EC Compound

Specific examples of anodic EC compounds that can be used in the present invention are given below. It should be noted that these are non-limiting examples of anodic EC compounds used in the present invention.

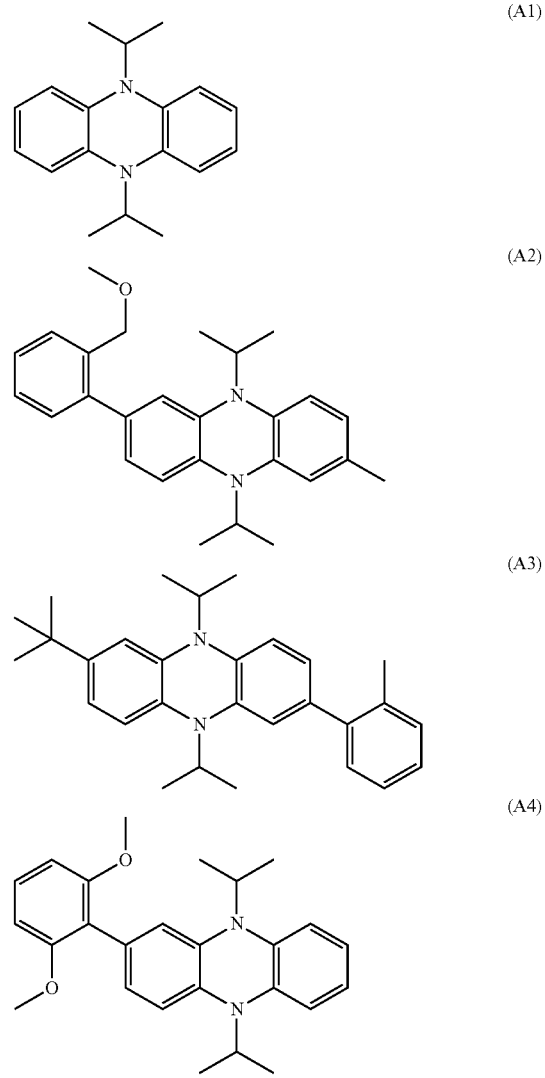

-continued

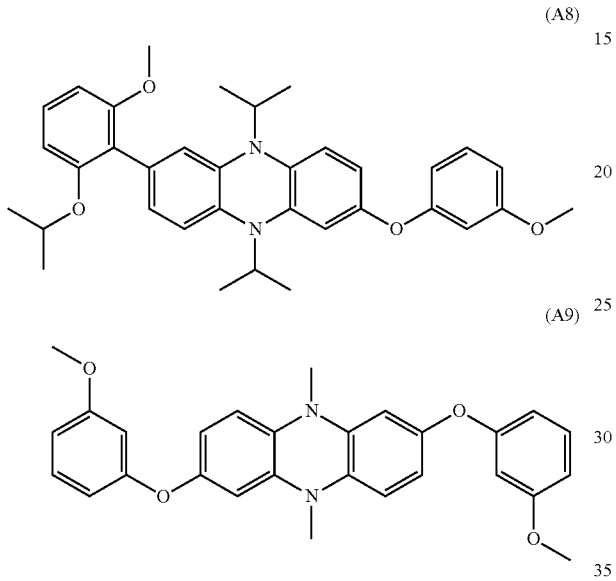

(A5)

(A8)

(A9)

For reference, specific examples of anodic EC compounds not satisfying the above condition (inequality (1)) are given below.

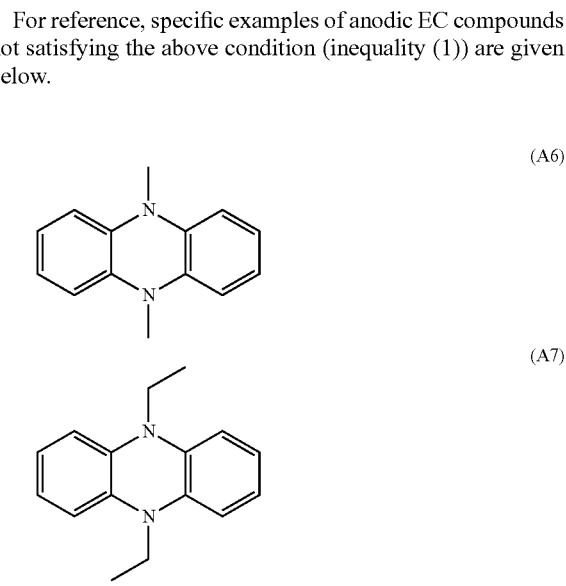

(A6)

(A7)

Table 1 summarizes the differences between solvation free energies of oxidized forms of the above anodic EC compounds in water and solvation free energies of the oxidized forms in octanol. Oxidized forms of the above anodic EC compounds (A1) to (A7) are each a colored form. The solvation free energies were calculated by the above-described method.

TABLE 1

| Compound | A1 | A2 | A3 | A4 | A5 | A8 | A9 | A6 | A7 |
|---|---|---|---|---|---|---|---|---|---|
| $G^{4+}_{H2O} - G^{4+}_{OcOH}$ (kcal/mol) | 35.1 | 44.6 | 46.6 | 46.8 | 51.4 | 53.7 | 44.2 | 29.7 | 32.9 |

Cathodic EC compound

Likewise, specific examples of cathodic EC compounds that can be used in the present invention are given below. It should be noted that these are non-limiting examples of cathodic EC compounds used in the present invention.

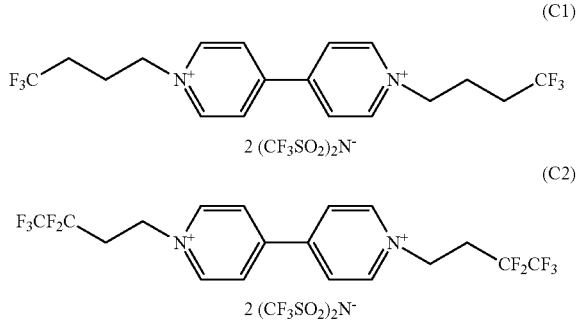

(C1)

2 (CF$_3$SO$_2$)$_2$N$^-$ (C2)

2 (CF$_3$SO$_2$)$_2$N$^-$

For reference, specific examples of cathodic EC compounds not satisfying the above condition, that is, not having a substituent containing an element that increases the density of organic compounds are given below.

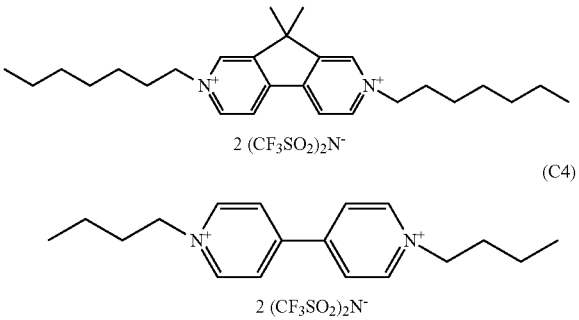

(C3)

2 (CF$_3$SO$_2$)$_2$N$^-$ (C4)

2 (CF$_3$SO$_2$)$_2$N$^-$

Preparation of EC Compounds

Of the above EC compounds, the anodic EC compound represented by formula (A1) was synthesized with reference to Patent Literature (U.S. Pat. No. 6,020,987). The anodic EC compounds represented by formulae (A2) to (A5), (A8), and (A9) were synthesized using a reaction represented by formula (A) below. (The second step was used for (A9).)

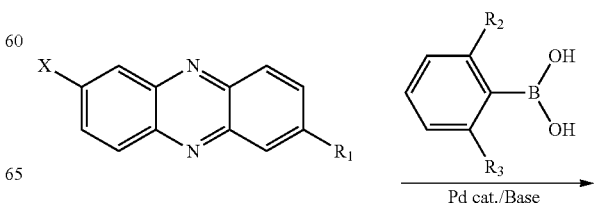

-continued

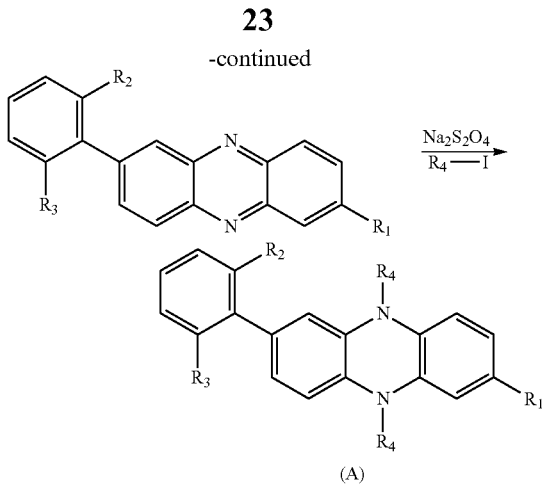

(A)

In formula (A), X is a halogen atom, $R_1$ is a hydrogen atom, an alkyl group, or a phenoxy group, $R_2$ and $R_3$ are each a hydrogen atom, an alkyl group, or an alkoxy group, and $R_4$ is a methyl group or an isopropyl group. In a first step, a combination of a substituted or unsubstituted halogenated phenazine and a phenylboronic acid having an alkyl group and an alkoxy group at the ortho positions or a boronic acid ester compound is subjected to a coupling reaction with a known Pd catalyst, whereby a precursor can be synthesized. Furthermore, in a second step, the phenazine ring is reduced and alkylated, whereby the anodic EC compounds represented by formulae (A2) to (A5) and (A8) can be synthesized.

For the compounds represented by formulae (A5), (A8), and (A9), a phenoxy group derivative needs to be introduced at the 2,7 position of the phenazine ring. The phenoxy group derivative can be introduced into the halogenated phenazine by a coupling reaction using phenol with a known Cu catalyst. As a specific example of the reaction of formula (A), a scheme for synthesizing the anodic EC compound represented by formula (A5) is shown by formula (B) below.

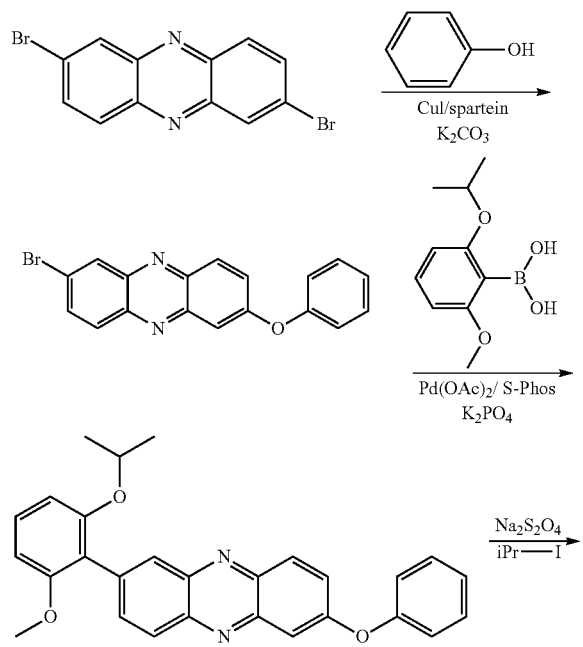

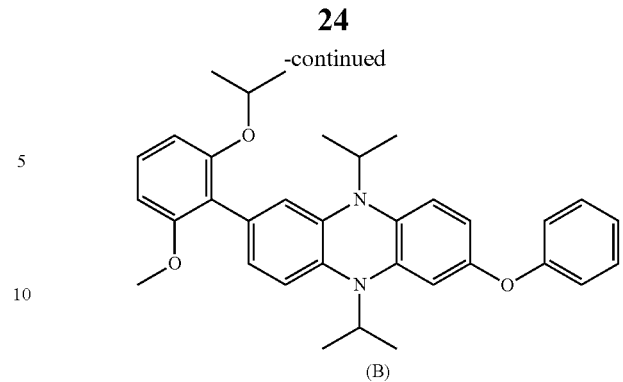

(B)

The anodic EC compound represented by formula (A5) can be synthesized, for example, according to the following procedure. First, a first-stage intermediate is synthesized. 2,7-Dibromophenazine and phenol were mixed together in DMSO, and dissolved oxygen was removed with nitrogen. Next, a CuI/Spartein complex and potassium carbonate were added, and the resulting mixture was refluxed for 8 hours. The reaction solution was concentrated under reduced pressure and purified by silica gel chromatography to obtain a first-stage intermediate as a yellow solid.

Next, the first-stage intermediate and 2-isopropoxy-6-methoxyphenylboronic acid were mixed together in a solvent mixture of toluene/1,4-dioxane, and dissolved oxygen was removed with nitrogen. Pd(OAc)2, 2-dicyclohexylphosphino-2',6'-dimethoxybiphenyl (S-Phos), and tripotassium phosphate were added, and the resulting mixture was refluxed for 15 hours. The reaction solution was concentrated under reduced pressure and separated and purified by silica gel chromatography to obtain a second-stage intermediate as a yellow solid.

Subsequently, the second-stage intermediate and 2-iodopropane were mixed together in a solvent mixture of acetonitrile/water, and dissolved oxygen was removed with nitrogen. Sodium hydrosulfite and potassium carbonate were added, and the resulting mixture was refluxed for 10 hours. The reaction solution was concentrated under reduced pressure and separated and purified by silica gel chromatography to obtain the anodic EC compound of formula (A5) as a solid. The results of $^1$H-NMR analysis of the anodic EC compound obtained are as follows.

$^1$H-NMR (deuterated acetone) δ (ppm): 7.35 (m, 2H), 7.19 (t, 1H), 7.06 (t, 1H), 6.99 (d, 2H), 6.8-6.65 (m, 6H), 6.49 (d, 1H), 6.42 (dd, 1H), 4.47 (sep, 1H), 4.17 (sep, 1H), 3.97 (sep, 1H), 3.71 (s, 3H), 1.51 (d, 6H), 1.46 (d, 6H), 1.18 (d, 6H).

The cathodic EC compounds represented by formulae (C1) to (C4) were synthesized using a reaction represented by formula (C) below.

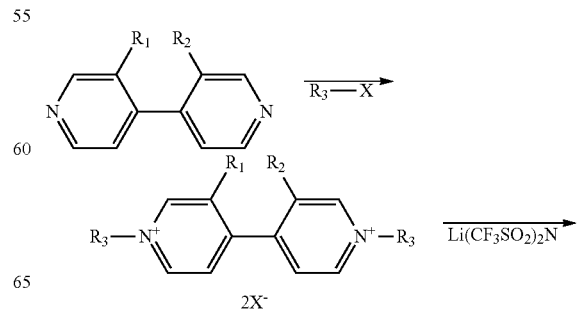

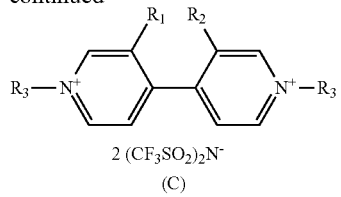

In formula (C), X is a halogen atom, $R_1$ and $R_2$ are each a hydrogen atom or an alkyl group, and $R_3$ is an alkyl group or a substituted alkyl group. Substituted or unsubstituted 4,4'-bipyridine is allowed to react with a halogenated (substituted/unsubstituted) alkyl compound, whereby a halogen salt of a compound of interest can be obtained. Furthermore, a salt exchange is performed using bis(trifluoromethanesulfonyl)imide lithium, whereby the compound of interest can be synthesized.

A synthesis example of the cathodic EC compound represented by formula (C1) will be described below as an example.

In a reaction vessel, 4,4'-bipyridine and an excess of 4,4',4''-trifluoroiodobutane were placed and allowed to react at 110° C. for 19 hours using DMF as a solvent. The precipitate was recovered and dissolved in water, and an excess of bis(trifluoromethanesulfonyl)imide lithium were added. The precipitate was recovered by filtration and dried to obtain the cathodic EC compound represented by formula (C1). The results of $^1$H-NMR analysis of the cathodic EC compound obtained are as follows.

$^1$H-NMR (DMSO) δ (ppm): 9.36 (d, 4H), 8.78 (d, 4H), 4.75 (t, 4H), 2.40 (m, 4H), 2.25 (t, 4H).

For the cathodic EC compound represented by formula (C4), a step of synthesizing a compound used as a raw material is necessary prior to the reaction of formula (C). A scheme for synthesizing the raw material is shown by formula (D) below.

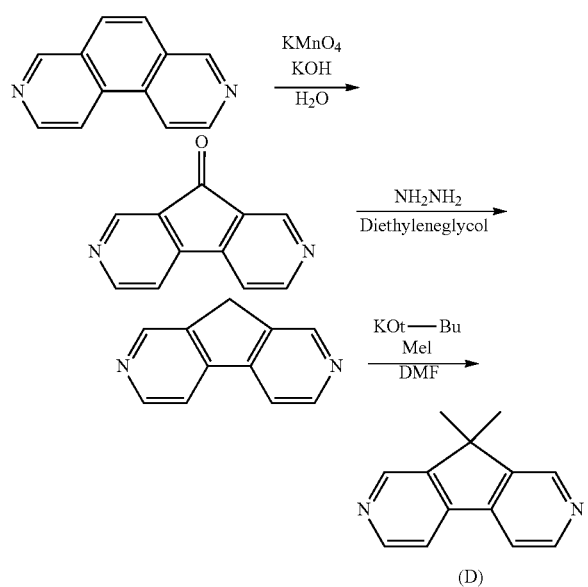

A method for synthesizing 9,9-dimethyl-2,7-diazafluorene, which is the raw material, will be described.

The raw material was synthesized with reference to Technical Literature (E. Botana, et al, Angew. Chem. Int. Ed. 46, 198-201 (2007).). In a reaction vessel, 3,8-phenanthroline, potassium hydroxide, and water were placed and heated at 90° C. Thereafter, a solution obtained by mixing water and potassium permanganate together and heating at 90° C. was added dropwise to the reaction solution. After reaction for 1 hour, a precipitated solid was filtered, extracted with chloroform, washed with water and saturated saline, dried, and concentrated to obtain a brown powder. The brown powder was separated and purified by silica gel chromatography to obtain a first intermediate as a yellow solid.

In a reaction vessel, the first intermediate, diethylene glycol, and hydrazine monohydrate were placed and allowed to react at 100° C. for 12 hours. Water was added to the resulting dark red suspension. The dark red suspension was extracted with dichloromethane, washed with water and saturated saline, dried, and concentrated to obtain a dark yellow solid. The dark yellow solid was separated and purified by silica gel chromatography to obtain a second intermediate as a yellowish brown solid.

In a reaction vessel, the second intermediate and DMF were placed and cooled in an ice bath. Thereafter, potassium tert-butoxide was added. The resulting mixture was stirred at the same temperature for 30 minutes, and iodomethane diluted in DMF was added dropwise. The resulting mixture was stirred at the same temperature for another 30 minutes and then allowed to react at room temperature for 3 hours. The resulting reddish brown suspension was added to a saturated sodium bicarbonate solution, extracted with ethyl acetate, washed with water and saturated saline, dried, and concentrated to obtain a dark yellow solid. The dark yellow solid was separated and purified by silica gel chromatography to obtain 9,9-dimethyl-2,7-diazafluorene as a beige solid.

The anodic EC compound represented by formula (A6), serving as a reference EC compound, was purchased and used as received. The anodic EC compound represented by formula (A7) was synthesized with reference to Patent Literature (U.S. Pat. No. 6,020,987).

Production of EC Element

An anodic EC compound and a cathodic EC compound were each selected from the EC compounds described above, and an EC element having a structure shown in FIG. 1 was produced by the following method.

Two transparent conductive glasses (10a and 10b) on which indium-doped tin oxide (ITO) films (electrodes 11a and 11b) were formed were provided and disposed such that the ITO films faced each other. The outer edges of the two transparent conductive glasses were then bonded to each other using a sealing member 13 containing spacer beads having a diameter of 50 μm. An anodic EC compound represented by any one of formulae (A1) to (A7) and a cathodic EC compound represented by any one of formulae (C1) to (C4) were dissolved in propylene carbonate each at a concentration of 0.1 mol/L. The solution was injected through an inlet (not illustrated) preliminarily formed in the transparent conductive glass 10b, whereby the space created by the two transparent conductive glasses (10a and 10b) and the sealing member 13 was filled with the solution. Thereafter, the inlet (not illustrated) was sealed with a sealing agent to obtain an EC element.

Evaluation of Vertical Color Separation

The above EC element having a rectangular element plane was combined with an automatic XZ stage with the long side of the EC element extending horizontally and the short side of the EC element extending vertically. Then, using a spectrometer including a light source, an optical fiber, a lens, and a spectroscope combined together, transmission spectra at points in the element plane of the EC element were measured continuously for 24 hours. The average spectrum of all the points in the plane was used as a reference spectrum, and the deviation of a spectrum at each point in the plane was evaluated using a value of d(ΔOD). The value of d(ΔOD) is as described above.

The types of color separation of the EC element include not only vertical color separation but also electrode color separation due to the resistance of the transparent conductive glasses. Specifically, a phenomenon may occur in which an anodic EC compound and a cathodic EC compound are colored strongly in the vicinity of power supply bus bars of an anode and a cathode, respectively. In the evaluation measurement of vertical color separation, a four-terminal alternation driving method was used in order to eliminate the influence of electrode color separation.

The four-terminal alternation driving method will be described below in detail. A power supply bus bar for the EC element was provided on each of the two long sides (horizontal direction) of each of the anode and the cathode so as to extend along the long sides. In other words, the anode and the cathode were each provided with two upper and lower power supply bus bars. Current application to the upper bus bar of the anode and the lower bus bar of the cathode and current application to the lower bus bar of the anode and the upper bus bar of the cathode were alternately performed. In this investigation, the cycle of alternate application was set to 1 Hz. The applied voltage was determined by adding an overvoltage of 0.15 V to the difference between the half-wave potential of the anodic EC material and the half-wave potential of the cathodic EC compound.

The half-wave potential of each EC compound was measured by performing cyclic voltammetry in a nitrogen atmosphere at 25° C. using an ITO electrode as a working electrode, a platinum wire as a counter electrode, and Ag/Ag$^+$ (PC, PF$_6$) as a reference electrode. In this measurement, propylene carbonate was used as a solvent, 0.1 M tetrabutylammonium hexafluorophosphate was used as a supporting electrolyte, the EC compound concentration was 1 mmol/L, and the sweep rate was 0.1 Vs$^{-1}$.

Evaluation Results

Table 2 shows the results of measurements of the degree of vertical color separation of EC elements in each of which an anodic EC compound represented by any one of formulae (A1) to (A7) and the cathodic EC compound represented by formula (C3) are used. The results in Table 2 correspond to the graph of FIG. 2. The results show that the degree of vertical color separation tends to decrease as the difference between a solvation free energy of an oxidized form of the anodic EC compound in water and a solvation free energy of the oxidized form in octanol increases. Specifically, when the solvation free energy difference is 35 kcal/mol or more, the degree of vertical color separation can be markedly reduced, and when the solvation free energy difference is 44 kcal/mol or more, the degree of vertical color separation can be more markedly reduced.

However, it was found that there is a limit to how effectively vertical color separation can be suppressed only by focusing on the solvation free energy difference $G^{4+}_{H2O} - G^{4+}_{OcOH}$ and selecting an anodic EC compound. Specifically, it was difficult to reduce the value of d(ΔOD) to 0.01 or less.

TABLE 2

| Compound | A1 | A2 | A3 | A4 | A5 | A8 | A9 | A6 | A7 |
|---|---|---|---|---|---|---|---|---|---|
| $G^{4+}_{H2O} - G^{4+}_{OcOH}$ (kcal/mol) | 35.1 | 44.6 | 46.6 | 46.8 | 51.4 | 53.7 | 44.2 | 29.7 | 32.9 |
| Maximum value of d(ΔOD) | 0.038 | 0.025 | 0.024 | 0.015 | 0.014 | 0.014 | 0.013 | 0.084 | 0.054 |

Table 3 shows the results of measurements of the degree of vertical color separation of EC elements in each of which the anodic EC compound represented by formula (A1) and a cathodic EC compound represented by any one of formulae (C1) to (C4) are used. Among the results in Table 3, the results of formulae (C1) and (C2) correspond to the graph of FIG. 3. These results show that the degree of vertical color separation can be decreased by introducing an element that improves the density of compounds into a substituent of a cathodic EC compound. Specifically, the degree of vertical color separation can be decreased by introducing fluorine into a substituent of a cathodic EC compound.

The above studies demonstrate that vertical color separation cannot be effectively suppressed such that the value of d(ΔOD) is as low as 0.01 or less until both the anodic EC compound and the cathodic EC compound are selected focusing on the above solvation free energy difference. More specifically, vertical color separation cannot be effectively suppressed such that the value of d(ΔOD) is as low as 0.01 or less until both the above two conditions (a) and (b) are satisfied.

TABLE 3

| Compound | C1 | C2 | C3 | C4 |
|---|---|---|---|---|
| Maximum value of d(ΔOD) | 0.0043 | 0.0058 | 0.038 | 0.012 |

According to the present invention, an EC element in which vertical color separation is suppressed can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An electrochromic element comprising: a first electrode; a second electrode; and an electrochromic layer disposed between the first electrode and the second electrode, the electrochromic layer containing a solvent, an anodic electrochromic compound, and a cathodic electrochromic compound,
   wherein the cathodic electrochromic compound has a substituent containing any one element selected from halogens, sulfur, boron, phosphorus, and silicon, and the electrochromic element satisfies inequality (1):

$$G^{A+}_{H2O} - G^{A+}_{OcOH} \geq 35 \qquad \text{inequality (1)}$$

where, in inequality (1), $G^{A+}_{H2O}$ represents a solvation free energy (kcal/mol) of an oxidized form of the anodic electrochromic compound in water, and $G^{A+}_{OcOH}$ represents a solvation free energy (kcal/mol) of the oxidized form of the anodic electrochromic compound in octanol.

2. The electrochromic element according to claim 1, wherein the electrochromic element further satisfies inequality (2):

$$G^{A+}_{H2O} - G^{A+}_{OcOH} \geq 44 \qquad \text{inequality (2)}.$$

3. The electrochromic element according to claim 1, wherein the cathodic electrochromic compound has a substituent containing a halogen.

4. The electrochromic element according to claim 1, wherein the cathodic electrochromic compound has a substituent containing fluorine.

5. The electrochromic element according to claim 1, wherein in the electrochromic layer, at least one of a concentration of the anodic electrochromic compound and a concentration of the cathodic electrochromic compound is 0.05 mol/L or more.

6. The electrochromic element according to claim 1, wherein the anodic electrochromic compound is a dihydrophenazine derivative.

7. The electrochromic element according to claim 1, wherein the cathodic electrochromic compound is a pyridine derivative.

8. The electrochromic element according to claim 7, wherein the cathodic electrochromic compound has a viologen skeleton.

9. The electrochromic element according to claim 8, wherein the cathodic electrochromic compound is a compound represented by general formula (11):

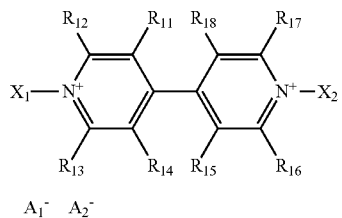

in general formula (11), $X_1$ and $X_2$ are each independently selected from an alkyl group, an aralkyl group, and an aryl group, the alkyl group, the aralkyl group, and the aryl group optionally having a substituent, $R_{11}$ to $R_{18}$ are each independently any one of a hydrogen atom, an alkyl group, an aralkyl group, an alkoxy group, an aryl group, a heterocyclic group, a substituted amino group, a halogen atom, and an acyl group, the alkyl group, the alkoxy group, the aralkyl group, the aryl group, and the heterocyclic group optionally having a substituent, $A_1$, and $A_2$, each independently represent a monovalent anion, and at least one of $X_1$, $X_2$, and $R_{11}$ to $R_{18}$ is a substituent containing any one element selected from halogens, sulfur, boron, phosphorus, and silicon.

10. The electrochromic element according to claim 1, wherein the solvent is a cyclic ether.

11. A lens unit comprising:
an optical filter including the electrochromic element according to claim 1; and
an image pickup optical system including a plurality of lenses.

12. An image pickup apparatus comprising:
an image pickup optical system including a plurality of lenses;
an optical filter including the electrochromic element according to claim 1; and
an image pickup element that receives light transmitted through the optical filter.

13. An image pickup apparatus to which an image pickup optical system including a plurality of lenses is attachable, the image pickup apparatus comprising:
an optical filter including the electrochromic element according to claim 1; and
an image pickup element that receives light transmitted through the optical filter.

14. A window member comprising:
a pair of substrates; and
the electrochromic element according to claim 1,
wherein the electrochromic element is disposed between the pair of substrates, and
the electrochromic element adjusts the amount of light transmitted through the pair of substrates.

15. An electrochromic element comprising: a first electrode; a second electrode; and an electrochromic layer disposed between the first electrode and the second electrode, the electrochromic layer containing a solvent, an anodic electrochromic compound, and a cathodic electrochromic compound,
wherein a difference between a solvation free energy of a colored form of the anodic electrochromic compound in water and a solvation free energy of the colored form of the anodic electrochromic compound in octanol is 35 kcal/mol or more, and
the cathodic electrochromic compound has a substituent containing any one element selected from halogens, sulfur, boron, phosphorus, and silicon.

* * * * *